United States Patent [19]
Mitsky et al.

[11] Patent Number: 5,510,253
[45] Date of Patent: Apr. 23, 1996

[54] PLANTS RESISTANT TO INFECTION BY PLRV

[75] Inventors: Timothy A. Mitsky, Chesterfield, Mo.; Cynthia L. Hemenway, Apex, N.C.; Nilgun E. Tumer, Princeton Junction, N.J.

[73] Assignee: Monsanto Company, St. Louis, Mich.

[21] Appl. No.: 326,297

[22] Filed: Oct. 20, 1994

Related U.S. Application Data

[63] Continuation of Ser. No. 12,688, Feb. 3, 1993, abandoned.

[51] Int. Cl.⁶ .............................. A01H 1/04; C12N 15/00; C07H 17/00
[52] U.S. Cl. .................. 435/172.3; 435/69.1; 435/240.4; 435/320.1; 536/23.72; 800/205; 800/DIG. 40; 800/DIG. 42
[58] Field of Search ........................... 800/205, DIG. 40, 800/DIG. 42; 536/23, 72; 435/69.1, 172.3, 320.1, 240.4

[56] References Cited

U.S. PATENT DOCUMENTS 4,970,168 11/1990 Tumer .................................. 435/317.1

OTHER PUBLICATIONS

Kawchuk et al (1990) Mol Plant–Microbe Int. 3(5): 301–307.
Kawchuk et al (1989) J. Gen Virol 70:783–788.
Audy et al. (1994) Mol Plant–Microbe Int 7(1):15–22.
Sanger et al (1990) Plant Mol Biol 14:433–443.
Vander Wilk (1989) FEBS Lett. 245 (1,2):51–56.
Golemboski et al (1990) Proc. Natl Acad Sci USA 87:6311–6315.
Sanger et al. (1990) *Plant Molecular Biology* 14:433–443. Characteristics of a strong promoter from figwort mosaic virus: comparison with the analogous 35S promoter from cauliflower mosaic virus and the regulated mannopine synthase promoter.
Kawchuk et al. (1991) *Molecular Plant Microbe Interactions* 4(3):247–253. Sense and antisense RNA–mediated resistance to potato leafroll virus in russet Burbank potato plants.
Kawchuk et al. (1990) *Molecular Plant Microbe Interactions* 3(5):301–307. Resistance in transgenic potato expressing the potato leafroll virus coat protein gene.
Kawchuk et al. (1989) *J. Gen Virol.* 70:783–788. Identification and characterization of the potato leafroll virus putative coat protein gene.
Van der Wilk et al. (1989) *FEBS Letters* 245(1,2):51–56. Nucleotide sequence and organization of potato leafroll virus genomic RNA.
Golemboski et al. (1990) *Proc. Natl. Acad. Sci. USA* 87:6311–6315. Plants transformed with a tobacco mosaic virus nonstructural gene sequence are resistant to the virus.
Carr et al. (1992) *Molecular Plant Microbe Interactions* 5(5):397–404. Resistance to tobacco mosaic virus induced by the 54–kDa gene sequence requires expression of the 54–kDa protein.
Donson et al. (1993) *Molecular Plant Microbe Interactions* 6(5):635–642. Broad resistance to tobamoviruses is mediated by a modified tobacco mosaic virus replicase transgene.
McFarlane and Davies (1992) *Proc. Natl. Acad. Sci. USA* 89:5829–5833. Plants transformed with a region of the 201–kilodalton replicase gene from pea early browning virus RNA1 are resistant to virus infection.
Taschner et al. (1991) *Virology* 181:445–450. Replication of an incomplete alfalfa mosaic virus genome in plants transformed with viral replicase genes.
Longstaff et al. (1993) *EMBO J.* 12(2):379–386. Extreme resistance to potato virus X infection in plants expressing a modified component of the putative viral replicase.
Anderson et al. (1992) *Proc. Natl. Acad. Sci. USA* 89:8759–8763. A defective replicase gene induces resistance to cucumber mosaic virus in transgenic tobacco plants.
Day et al. (1991) *Proc. Natl. Acad. Sci. USA* 88:6721–6725. Expression of an antisense viral gene in transgenic tobacco confers resistance to the DNA virus tomato golden mosaic virus.
Braun and Hemenway (1992) *The Plant Cell* 4:735–744. Expression of amino–terminal portions or full–length viral replicase genes in transgenic plants confers resistance to potato virus X infection.
Audy et al. (1992) Abstract, *Canadian J of Plant Pathology* 14:240. Transformation of potato and tobacco with modified replicase genes of potato viruses Y and leafroll.
Audy et al. (1994) *Molecular Plant–Micobe Interactions* 7(1):15–22). Replicase–mediated resistance to potato virus Y in transgenic tobacco plants.

*Primary Examiner*—David T. Fox
*Assistant Examiner*—Elizabeth F. McElwain
*Attorney, Agent, or Firm*—Grace L. Bonner; Dennis R. Hoerner, Jr.; Richard H. Shear

[57] ABSTRACT

An isolated DNA sequence which codes for a PLRV replicase gene is disclosed herein. A method for providing resistance to infection by a virus by expressing a replicase gene in plants is also disclosed, as are transgenic potato plants and tubers containing the replicase gene.

21 Claims, 12 Drawing Sheets

CONTROLS

18685

18658

18643

18644

Average Percent Infection (Visual Rating)

Average Percent Infection (Visual Rating)

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 3901 base pairs
        ( B ) TYPE: nucleic acid
        ( C ) STRANDEDNESS: double
        ( D ) TOPOLOGY: linear ( i i ) MOLECULE TYPE: cDNA (genomic)

( x i ) SEQUENCE DESCRIPTION: SEQ ID NO:1:

-continued

```
GGTACCATGG AGCAAGCGAG CTTAATTTAC GGCTATAATC ATGAACAGAT TTACCGCATA      60
TGCCGCTCTT TTCTTCATGT TCTCCCTTTG CTCAACTGCA AAAGAGGCAG GATTTCTACA     120
TCCGGCCTTC AACTTCCGAG GCACCTCCAC TATAAGTGCC TCGAGTGGGG ATTACTCTGC     180
GGCTCCCTCC CCACTATACA AATCGAGGGT CCTACCATCG TCATTAAACT TGACGACCCA     240
ACCACTGCCG CCACTTACAG ATCGGAGCTA CTACGAGTTA GTTCAAGCTC TTATATCCAA     300
AATGCGGCTG GATTGTCAAA CGGTTGGGGA CATGACATGG AGGCATTTGT CAGAAATGCT     360
ATTTGCCTCC TGGAACTCCG TGAAAGAAGT ATCCCTCAAA GCGGCCTCCG TGACCTTATG     420
GGCAATTATC AACATTTGGT TCGGTCTCTA TTGGACGCTT GCATGGTTGA TCACTTTGTT     480
CCTCTGGACT TTCAGCATAG AAGCCTTATG CTTAATTTTG CTCGGTTGTA TAACCAGCTT     540
GATCTACAAG GGCGCGCTAA GTCTTTCAGA GCACTTACCG GTTTTCCTGT TTATGTCCCC     600
TCTGAAGATT ATTTGGAGGG CAGCTTTCTC CAAAAGGAAT TACAAGAATG AGAGGGCTGT     660
GGAAGGATAC AAAGGGTTTT CGGTCCCACA GAAACCGCCA AAGTCTGCCG TAATTGAACT     720
ACAACATGAA AACGGCAGCC ATCTCGGGTA CGCGAACTGC ATTCGCTTGT ACAGTGGAGA     780
GAACGCCTTG GTGACAGCTG AACACTGTCT AGAAGGCGCT TTCGCAACGT CGTTGAAAAC     840
TGGAAACAGG ATTCCGATGT CGACTTTCTT TCCCATTTTC AAAAGTGCCC GTAATGATAT     900
CTCCATACTA GTGGGTCCAC CCAACTGGGA AGGTCTACTA TCAGTCAAAG GAGTCCATTT     960
CATTACAGCT GATAAAATCG GCAAAGGTCC TGCCTCTTTC TACACTCTTG AGAAAGGGGA    1020
GTGGATGTGC CATAGTGCCA CCATAGATGG AGCCCATCAC CAGTTCGTGT CTGTTTTATG    1080
CAACACTGGA CCCGGATATT CCGGAACAGG GTTTTGGTCT TCAAAGAATC TGCTTGGTGT    1140
GCTTAAAGGC TTCCCACTGG AAGAGGAGTG TAACTACAAT GTTATGTCTG TTATACCCTC    1200
GATCCCAGGA ATCACTTCCC CAAATTATGT GTTTGAGTCG ACCGCCGATA AGGCCGCGT    1260
CTTCTCGGAT GAAACTGTGA AGAACTAGA GCGGGAAGCA AAGAAGCCG TCATGAAGCT     1320
TGCCAAATTT AAATCACTCG CCGGCAAGAA CTGGGCTGAT GATTATGACT CCGATGAGGA    1380
TTACGGTCTG GAGAGAGAGG CTGCAACAAA TGCGCCCGCA GAGAAACTG CTCAAACAAA     1440
CTCAGCAGAG AAGACTGCTC CATCAACTTC AGCAGAGAAA ACTGCTCCAA CAAACAAGCC    1500
TTTAAATGGG CAAGCGGCAC CGCGCAAAAC AAACGGCAAC TCCGACATCC CCGACGCCGC    1560
TACGAGCGCA CCACCAATGG ACAAAATGGT CGAACAGATC ATCACAGCTA TGGTGGGGAG    1620
AATCAATCTC TCGGAGATAG AGGAGAAGAT AGTGAGCAGG GTGTCTCAGA AAGCCCTGCA    1680
GAAGCCCAAA CAAAGAAGC GCGGAAGGCG TGGAGGGAAG AACAAGCAAA ACAGTTCACC     1740
TCCTACTTCA ACGCAATCTA CAAGTGGGGT GCCCAAGAAG GAGGTCTGCC CCCTAGGCTT    1800
CAGGAAGTGC GGTACATCCC CGGCTACTAC CACCCCCGCA CCAGAGGCGA ACCCAGTGG     1860
GGGCAAAAAC TCTGCCAAGT TCATCCCGAG CTGGCGGAGA AAACAGCAGG ATTCGGCTGG    1920
CCAAAAGCCG GATCTGAAGC TGAGCTCCAA AGCCTGAATC TACAGGCTGC CAGGTGGCTC    1980
CAACGCGCGG AGTCGGCCAC TATCCCTGGC GCAGAAGCAA GAAAGCGCGT GATTGAGAAA    2040
ACAGTGGAGG CATACAGAAA TTGTGTAACT AACGCCCCAC TGTGCTCCCT TAAATCCAAA    2100
CTGGATTGGA CTGGCTTTCA ACAAGATATC CGTGAAGCAG TCCAGTCCCT TGAGCTAGAC    2160
GCTGGTGTAG GCATCCCCTA TATCGCGTAT GGCCTCCCCA CACACCGAGG ATGGGTTGAG    2220
GACCATAAGC TTCTCCCAGT ACTCACTCAG CTGACCTTTG ACCGACTACA GAAGATGTCA    2280
GAGGCCAGCT TGAGGATAT GAGCGCAGAA GAGCTGGTTC AAGAAGGGCT CTGTGATCCT    2340
ATCAGACTAT TTGTCAAAGG AGAGCCCCAC AAACAGAGCA AACTCGATGA AGGCCGCTAC    2400
```

| | | | | | | |
|---|---|---|---|---|---|---|
|CGCCTCATCA|TGTCTGTTTC|CTTGGTGGAT|CAACTGGTAG|CCCGGGTTCT|GTTCCAAAAT|2460|
|CAGAACAAAA|GGGAAATTTC|CCTGTGGAGG|TCTGTGCCTT|CCAAACCCGG|TTTTGGCCTT|2520|
|TCAACTGACA|CTCAAACTGC|TGAATTCTTG|GAGTGTCTCC|AAAAGGTGTC|TGGAGCGCCA|2580|
|TCTGTGGAAG|AATTGTGTGC|AAATCACAAG|GAGTACACGC|GCCCAACCGA|CTGTTCCGGT|2640|
|TTCGACTGGT|CAGTCGCGTA|TTGGATCCTG|GAGGATGATA|TGGAGGTGAG|AAATCGCCTG|2700|
|ACATTTAATA|ACACCCAGCT|CACCAAGCGC|CTTCGGGCTG|CCTGGTTGAA|GTGCATAGGA|2760|
|AACTCCGTCC|TGTGCCTGTC|CGATGGCACT|TTACTTGCCC|AAACTGTTCC|CGGTGTGCAA|2820|
|AAGAGCGGAA|GTTACAATAC|AAGTTCCTCC|AACTCTAGAA|TCCGGGTTAT|GGCTGCCTAT|2880|
|CACTGTGGCG|CCGACTGGGC|AATGGCCATG|GGGGACGATG|CTCTCGAAGC|CCCCAACTCC|2940|
|GACCTAGAGG|AGTATAAAAC|TCTAGGTTTC|AAAGTCGAGG|TAGGTCGAGA|ACTCGAATTC|3000|
|TGTTCACACA|TCTTCAGAAA|TCCGACCCTC|GCCGTTCCGG|TCAACACCAA|CAAAATGCTT|3060|
|TACAAGTTGA|TCCATGGTTA|TAATCCGGAA|TGTGGCAATC|CAGAAGTGAT|TCAAAACTAT|3120|
|CTGGCTGCAG|TATTCTCTGT|GCTGCAGGAA|CTCCGACACG|ATCGTGAGCT|CGTTGCCAAG|3180|
|CTCCACCAGT|GGTTGGTTCC|GAGTGCCACC|ACAAAAGAAC|ACTGAAGGAG|CTCACTATAA|3240|
|CTAGCCAAGC|ATACGCGAGT|TGCAAGCATT|GGAAGTTCAA|GCCTCGTTAC|ATCAACCGGA|3300|
|CAAAATAGAT|TTAAAATTCT|TAGCGGGATT|TGCTTTAGGA|TTCTCATCCG|CAATCCCATT|3360|
|TTCAGTAGCC|GGTTTATATT|TAGTTTACCT|AAAGATTTCC|TCCCACGTGC|GATTAATCGT|3420|
|TAATGAGTAC|GGTCGTGGTT|AAAGGAAATG|TCAATGGTGG|TGTACAACAA|CCAAGAAGGC|3480|
|GAAGAAGGCA|ATCCCTTCGC|AGGCGCGCTA|ACAGAGTACA|GCCAGTGGTT|ATGGTCACGG|3540|
|CCCCTGGGCA|ACCCAGGCGC|CGAAGACGCA|GAAGAGGAGG|CAATCGCCGC|TCGAGAAGAA|3600|
|CTGGAGTTCC|CCGAGGACGA|GGCTCAAGCG|AGACATTCGT|GTTTACAAAG|GACAACCTCG|3660|
|TGGGCAACTC|CCAAGGAAGT|TTCACCTTCG|GGCCGAGTGT|ATCAGACTGT|CCGGCATTCA|3720|
|AGGATGGAAT|ACTCAAGGCC|TACCATGAGT|ATAAGATCAC|AAGTATCTTA|CTTCAGTTCG|3780|
|TCAGCGAGGC|CTCTTCCACC|TCCTCCGGAT|CCATCGCTTA|TGAGTTGGAC|CCCCATTGCA|3840|
|AAGTATCATC|CCTCCAGTCC|TACGTCAACC|AGTTCCAAAT|TACAAGGGC|GCCATGGTAC|3900|
|C| | | | | |3901|

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGAGGTGCCT CGGAAGTTGA AGGCCGG  27

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

```
TCTGTTCATG ATAGATCTCG TAAATTAAGC TC                                              3 2
```

( 2 ) INFORMATION FOR SEQ ID NO:4:

( i ) SEQUENCE CHARACTERISTICS:
    ( A ) LENGTH: 197 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

```
GGTACCGGAT CCAGCTTTCG TTCGTATCAT CGGTTTCGAC AACGTTCGTC AAGTTCAATG      60

CATCAGTTTC ATTGCGCACA CACCAGAATC CTACTGAGTT CGAGTATTAT GGCATTGGGA     120

AAACTGTTTT TCTTGTACCA TTTGTTGTGC TTGTAATTTA CTGTGTTTTT TATTCGGTTT     180

TCGCTATCGA ACTGTGA                                                    197
```

( 2 ) INFORMATION FOR SEQ ID NO:5:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:5:

```
CGGTGCCGCT TGCCCAATTC AAGGGCTTGT TGTTG                                 36
```

PLANTS RESISTANT TO INFECTION BY PLRV

This is a Continuation of application Ser. No. 08/012,688, filed Feb. 3, 1993 now abandoned.

FIELD OF THE INVENTION

The present invention is related to the genetic engineering of plants. In particular the present invention relates to genetically modified plants which are resistant to viruses.

BACKGROUND OF THE INVENTION

Many agriculturally important crops are susceptible to infection by plant viruses. These viruses can seriously damage a crop and drastically reduce its economic value to the grower. This eventually leads to a higher cost for the consumer. Attempts to control or prevent infection of a crop by a plant virus have been made, yet vital pathogens continue to be a significant problem in agriculture.

Scientists have recently developed means to produce virus resistant plants using genetic engineering techniques. Such an approach is advantageous, in that the means for providing the protection is incorporated into the plant itself and is passed on to its progeny. A host plant is resistant if it possesses the ability to prevent infection, to suppress or retard the multiplication of a virus, and to suppress or retard the development of pathogenic symptoms. "Resistant" is the opposite of "susceptible", and definitions of the terms are described in Cooper and Jones, 1983. Several different types of host resistance to viruses are recognized. The host may be resistant to: (1) establishment of infection, (2) virus multiplication, or (3) viral movement.

Genes which interfere with the process of virus replication and/or infection may be expressed in transgenic plants to protect against viral disease. It has previously been shown that expression of a plant virus capsid protein, which is termed the coat protein (CP), in a plant can confer resistance to the homologous virus and to related viruses (Abel et. al., 1986; Turner et. al., 1987: Cuozzo et al., 1988; Hemenway et. al., 1988; Stark et. al., 1989; Lawson et. al. 1990; Kaniewski et. al., 1990). In these studies, resistance to virus disease is defined as either reduced incidence of infection, delayed symptom development, reduced virus replication or vital antigen levels, or slower to no systemic virus movement. Expression of the virus coat protein in these transgenic plants may be responsible for the observed effects in the reduction of virus disease by an as yet undetermined mechanism (Abel et. al.,1986; van Dun et. al., 1988-A). This type of protection against viral infection is termed coat protein-mediated resistance.

Even though coat protein-mediated vital resistance has proven to be useful in a variety of situations, it may not always be the most effective means for providing vital resistance. In such instances, other methods maybe useful for conferring viral resistance to plants. Other techologies have been demonstrated or proposed which affect virus or disease development. Examples of these are: antisense coat protein (Cuzzo et. al., 1988), satellite RNA (Harrison et. al., 1987), ribozymes (Walbot et. al., 1988), defective interfering molecules (Morch 1987), vital nonstructural genes (Golemboski et. al., 1990),( Braun et al., 1992) antibodies (Hiatt 1990), PR proteins (Bol et. al., 1990) and antiviral proteins (Irvin et. al., 1980).

A fragment of the putative replicase gene from tobacco mosaic virus (TMV), a vital nonstructural gene, recently has been found to provide resistance against TMV when expressed in tobacco plants (Golemboski et. al., 1990). In TMV, two proteins, the 183 kilodalton (kDa) and 126 kDa proteins, have been speculated to be replicase components, as the expression of both proteins are necessary for normal multiplication in tobacco plants (Ishikawa et. al., 1986). In addition, these two proteins contain evolutionarily conserved motifs, such as the NTP binding motif and the GDD domain, that are often found in other known RNA dependent RNA polymerases or replicase genes (Koonin, 1991). The NTP binding motif is the amino acid sequence G-X-X-X-X-G-K-X' where G is glycine, X is any amino acid, and X' is usually a serine (S) or threonine (T). (Gorbalenya et. al., 1988) The GDD motif is a larger domain, which is characterized by the presence of three invariant residues: glycine (G), followed by two aspartic acid (D) residues. GDD domains are often found in replicase proteins and are believed to be involved in catalytic function (Hodgman, 1988). The 183 kDa protein is produced by a translational read-through of the 126 kDa termination codon (TAG). The 126 kDa protein contains the NTP binding motif. The 183 kDa protein contains both the NTP and GDD motifs. The region of the TMV genome that conferred resistance was the read-through portion of the 183 kDa putative replicase gene. This read-through portion has the coding capacity for a 54 kDa protein. The GDD domain is located within the 54 kDa and 183 kDa protein sequence. For a number of years, it has been speculated that the 54 kDa protein is made as a separate gene product. To determine the function of this putative gene, Golemboski et. al. (1990) transformed tobacco with this sequence, and unexpectedly found that the transgenic plants were resistant to TMV. Plants transformed with the gene encoding the 126 kDa protein were unprotected. No data were reported on the 183 kDa read-through protein.

The mechanism of the observed resistance by expressing a truncated form of the replicase (the GDD domain) is unclear. It has recently been demonstrated in the case of the TMV 54 kDa read-through protein (GDD domain) that expression of the protein is required for the observed resistance (Carr et. al., 1992.).

Others have conducted protection experiments with transgenic plants expressing components of non-structural viral proteins. For Example, van Dun et. al. (1988) analyzed protection in tobacco plants expressing either of two genes encoding proteins involved in the replication of alfalfa mosaic virus (AlMV). These plants were transformed with cDNA's for RNAs 1 or 2 of AlMV, which encode proteins P1 and P2, respectively. The polypeptides, P1 and P2, encoded by these RNAs have amino acid similarities to other viral replicases, and both RNAs are known to be essential for replication. The NTP and GDD motifs for AlMV reside on different RNAs and consequently different proteins. Specifically, P1 contains the NTP binding motif and P2 contains the GDD motif. Plants expressing either RNA1 or RNA2 were unprotected against infection by AlMV. In addition, plants expressing both RNAs 1 and 2 were also unprotected against infection by AlMV (Taschner et. al., 1991).

Buck et. al. (PCT publication WO 92/03539) have described the use of various techniques to prevent the expression or function of a cucumber mosaic viral replicase in order to provide viral resistance in plants. The techniques employed or disclosed in this publication to accomplish resistance included: (1) antisense technology (wherein a complementary RNA to that coding for the full length replicase can be expressed); (2) expression of a gene coding for the production of an antibody specific for one of the three virally-encoded components of the replicase (viral encoded polypeptides P1a and P2a, and polypeptide P50 from tobacco); and (3) expression of a ribozyme specific for the RNA coding for one of the components of the replicase.

Potato leafroll virus (PLRV) is a member of the luteovirus plant virus group. PLRV is a positive-sense, single-stranded RNA virus. To form a vital particle, the viral RNA is encapsidated by the coat protein to give the characteristic isometric shape typical of viruses in the luteovirus group. Other members of the luteovirus group to which the present invention may be applied are: barley yellow dwarf virus, bean leaf roll, beet western yellows, carrot red leaf, groundnut rosette assistor, Indonesian soybean dwarf, soybean dwarf, and tobacco necrotic dwarf. Other possible members include beet yellow net, celery yellow spot, cotton anthocyanosis, filaree red leaf, milk vetch dwarf, millet red leaf, Physalis mild chlorosis, Physalis vein botch, raspberry leaf curl, tobacco vein distorting, tobacco yellow net, and tobacco yellow vein assistor.

PLRV RNA posesses a genome-linked proteinaceous unit at the 5' terminus and the 3' end does not contain a poly A tail. (Mayo et. al., 1982). The PLRV genomic RNA replicates through RNA intermediates in a DNA-independent fashion. PLRV RNA has six open readings frames (ORFs) (FIG. 1). The organization of the PLRV genome is reviewed in Martin et. al. (1990). In the 5' half of genomic RNA, a small ORF (ORF1) which encodes a 28 kDa protein is followed by two large ORFs (ORF 2a and ORF 2b), which may code for a 70 kDa and a 67 kDa protein, respectively. ORF2a and ORF2b is proposed to encode a putative replicase protein by virtue of its sequence similarity to other known replicase genes. In particular, ORF2a and ORF2b contain the motifs characteristic of NTP domain (Habili et. al., 1989) and RNA polymerases (Kamer et. al., 1984). ORF2b contains the GDD motif often found in replicase proteins and is believed to be involved in catalytic function. Henceforth we refer to the PLRV open reading frames 2a and 2b as the putative replicase or replicase. In PLRV isolate LR-7 Washington, ORF 2a and ORF 2b overlap by 579 nucleotides. Because ORF 2b lacks an AUG translational start codon in this region, it is postulated that ORF 2b is expressed by ribosomal frameshifting of ORF 2a (Mayo et. al., 1989).

A 2.3 kb subgenomic RNA transcribed from the minus strand message as part of the normal infection cycle is responsible for the translation of ORF3 (the coat protein (CP) gene), ORF4 (17 kDa putative nucleic acid binding protein (Tacke et. al., 1991) and ORF5 (56 kDa read-through protein, Bahner et. al., 1990). The CP gene is separated from a 56 kDa ORF by an amber stop codon (TAG). There is evidence that the 56 kDa protein is translated by suppression of the CP gene amber stop codon (Bahner et. al., 1990). Thus the 56 kDa ORF is expressed as a read-through product in a similar manner as the TMV 183 kDa protein.

The host range of PLRV is limited to members of the Solanaceae family of which potato, tobacco, tomato and peppers are important members. Commercially important potato cultivars to which the present invention may be applied include but are not limited to: Russet Burbank, Shepody, Atlantic, Norchip, and Superior. The host range of other luteoviruses may be more extensive. For example, the host range of beet western yellow virus includes 23 dicotyledenous families, and may affect the following crops: sugar beet, table beet, spinach, lettuce, soybean, broccoli, cauliflower, radish, turnip, pea, broad bean, chickpea, flax, sunflower, mustard, clover, cabbage:, swede, rape, crambe, pepper, pumpkin, watermelon, cucumber, tomato, etc. Additionally, the host range of barley yellow dwarf virus is limited to Gramineae, which would include barley, oats, wheat, rice, corn rye.

PLRV is transmitted in a persistent manner by aphids. One of the most serious viral problems in the potato industry is infection of the potato crop with potato leafroll virus (PLRV). Infection of potato by PLRV causes a reduction in both quality and yield of the potato crop, thus resulting in substantial economic losses. In Russet Burbank potato, the tuber symptom of PLRV infection is a phloem necrosis called "net necrosis". The virus induces a necrosis of the phloem as a primary pathological change (Shepardson et. al., 1980). This necrosis affects the processing quality of the potato and economically impacts the potato grower by reducing the value of the crop. Economic losses caused as a result of PLRV infection have been estimated to be approximately 5% of the world potato crop. Current management of PLRV infection of a crop involves the use of insecticides to control the aphids that transmit the virus, but this method of control is expensive, potentially dangerous to the environment, and not totally effective.

As can be seen from the foregoing discussion, potato leafroll virus infection of various plants is a serious problem encountered in agriculture today. Thus, it would be a significant contribution to the art to develop an alternative method to those currently available that is effective for conferring viral resistance to plants.

SUMMARY OF THE INVENTION

It is an object of the present invention to provide a DNA molecule which comprises:

(a) a promoter region which functions in plant cells to cause the production of an RNA sequence; which is operably linked to (b) a structural gene encoding a potato leafroll virus replicase; which is operably linked to (c) a 3' non-translated region which functions in plant cells to cause the termination of transcription and the addition of polyadenylated ribonucleotides to the 3' end of the transcribed mRNA sequence.

It is yet another object of the present invention to provide a method for providing resistance to infection by potato leafroll virus in a susceptible Solanaceae plant which comprises:

(a) transforming plant cells with a DNA molecule which comprises:

(i) a promoter region which functions in plant cells to cause the production of an RNA sequence; which is operably linked to (ii) a structural gene encoding a potato leafroll virus replicase; which is operably linked to (iii) a 3' non-translated region which functions in plant cells to cause the termination of transcription and the addition of polyadenylated ribonucleotides to the 3' end of the transcribed mRNA sequence;

(b) regenerating said plant cells to provide a differentiated plant; and (c) selecting a transformed plant which expresses the potato leafroll virus replicase gene at a level sufficient to render the plant resistant to infection by said potato leafroll virus.

It is a further object of this invention to provide a method for providing reduction in net necrosis resulting from infection by potato leafroll virus in a susceptible Solanaceae plant which comprises:

(a) transforming plant cells with a DNA molecule which comprises:

(i) a promoter region which functions in plant cells to cause the production of an RNA sequence; which is operably linked to (ii) a structural gene encoding a potato leafroll virus replicase; which is operably linked to (iii) a 3' non-translated region which functions in plant cells to cause the termination of transcription and the addition of polyadenylated ribonucleotides to the 3' end of the transcribed mRNA sequence;

(b) regenerating said plant cells to provide a differentiated plant; and (c) selecting a transformed plant which expresses the potato leafroll virus replicase gene at a level sufficient to render the plant resistant to infection by said potato leafroll virus.

It is still a further object of the present invention to provide a virus resistant transformed Solanaceae plant which contains in its genome a DNA molecule which comprises:

(a) a promoter region which functions in plant cells to cause the production of an RNA sequence; which is operably linked to (b) a structural gene encoding a potato leafroll virus replicase; which is operably linked to (c) a 3' non-translated region which functions in plant cells to cause the termination of transcription and the addition of polyadenylated ribonucleotides to the 3' end of the transcribed mRNA sequence.

Yet another object of the present invention is to provide a virus resistant transformed Solanaceae plant cell which contains in its genome a DNA molecule which comprises:

(a) a promoter region which functions in plant cells to cause the production of an RNA sequence; which is operably linked to (b) a structural gene encoding a potato leafroll virus replicase; which is operably linked to (c) a 3' non-translated region which functions in plant cells to cause the termination of transcription and the addition of polyadenylated ribonucleotides to the 3' end of the transcribed mRNA sequence.

Other objects, aspects, and advantages of the present invention will be apparent to those skilled in the art from the following description, EXAMPLE, and claims.

DETAILED DESCRIPTION OF THE INVENTION

Figure 1:
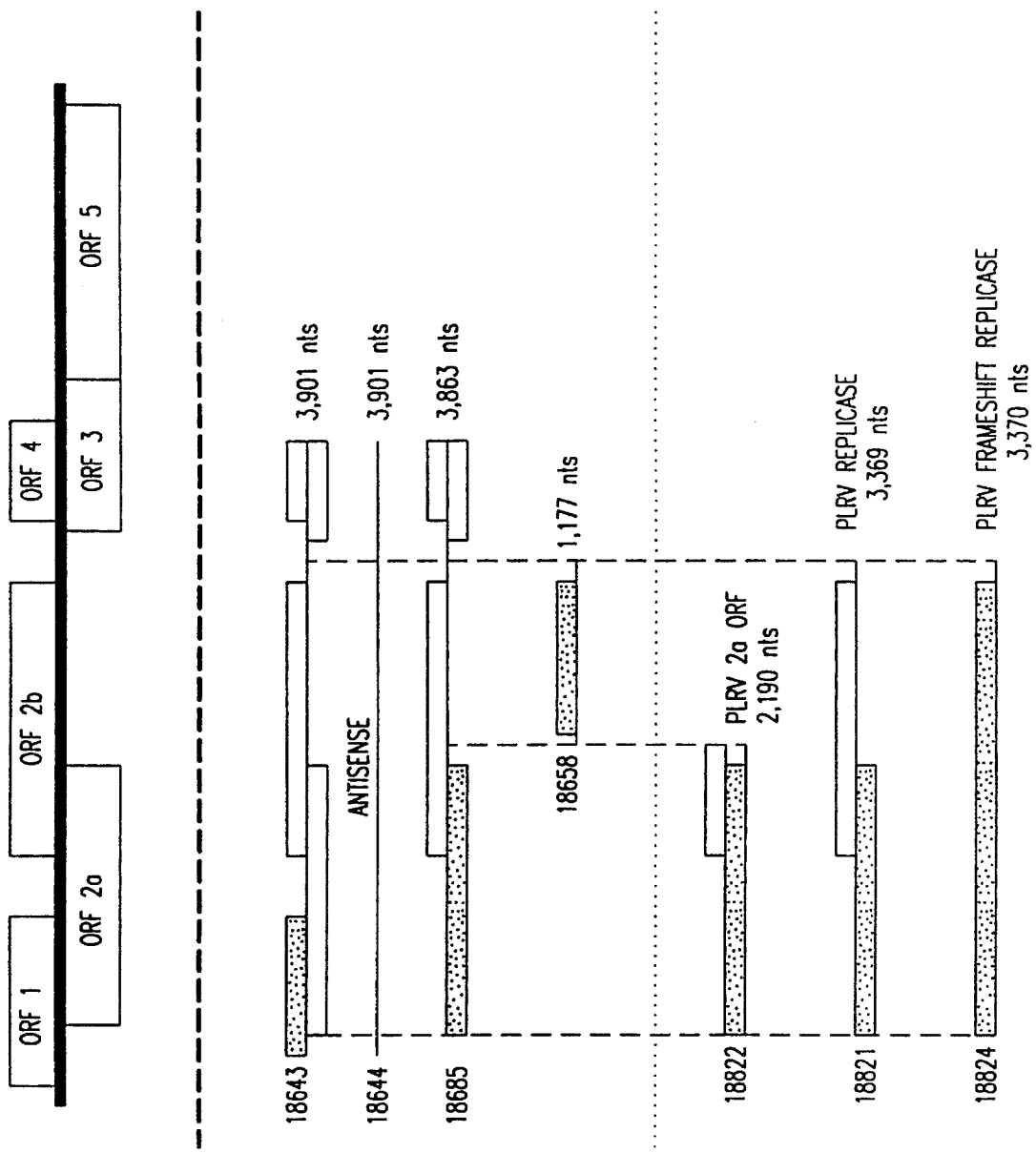
FIG. 1 illustrates the genomic organization of PLRV.

The viral resistance conferred to plants of the present invention is provided by the expression in plants of an isolated DNA sequence comprising nucleotides encoding a putative potato leafroll virus replicase. A cDNA sequence (SEQ ID NO. 1) encoding ORF2a and ORF2b of the PLRV genome and 666 nucleotides (nts) 3' to the termination codon of ORF2b (TGA) was prepared that provides resistance to infection by PLRV in plants expressing the RNA of SEQ ID NO. 1 and presumably the encoded protein or proteins at a sufficient level. Plant expression vectors or pMON vectors containing SEQ ID NO. 1 or modifications to SEQ ID NO. 1 are described in the EXAMPLE. It is believed that ORF2a/2b of the PLRV genome functions as a RNA dependent RNA polymerase (replicase) gene in plants infected with PLRV (van der Wilk et. al., 1989).

A potato leafroll virus replicase gene may be isolated from a cDNA library made from RNA recovered from purified potato leafroll virions as described in the EXAMPLE. The cDNA library may be constructed in a number of ways known to those of skilled in the art. The cDNA sequence of an exemplary replicase gene derived from the exemplified potato leafroll virus isolate is 3,184 nucleotides in length and corresponds to nt 41–3,225 in SEQ ID NO. 1.

A PLRV replicase gene or SEQ ID NO. 1 isolated from any of the various PLRV strains or isolates can be used in the present invention. The corresponding replicase gene from any PLRV strain consists of two overlapping ORFs, which follow the most 5' ORF (ORF1) of the viral genome which encodes a putative 28 kDa protein. The amino acid sequence of reported PLRV replicase ORFs exhibit a high degree of similarity when compared to other replicase genes from PLRV isolates in geographically remote locations. (Habili et. al., 1989.)

The full length putative replicase protein (ORF2a and ORF2b) is encoded by a −1 frameshift. The frameshift site has been identified as the heptanucleotide sequence UUUAAAU. This −1 frameshift occurs starting at nucleotide (nt) 1,501 in SEQ ID NO. 1 generating a 110 kDa frameshift protein containing both the NTP domain and the GDD domain. Experimentally, it has been shown that the frameshift occurs at a frequency of ≈1%. (Prüfer et. al., 1992.). For example, for every 100 2a proteins (70 kDa) translated in an infected cell, there will be one frameshifted (2a/2b) (110 kDa) protein translated. It is expected that the putative replicase clone (SEQ ID NO. 1) expressed in plants will frameshift by its natural mechanism, thereby encoding a full length 110 kDa 2a/2b putative replicase protein.

Because the mechanism of replicase-mediated resistance in not known, several plant gene expression vectors were designed to generate resistance to PLRV. These approaches are expression of a full length replicase gene (ORF 2a/2b), expression of a truncated replicase domain (GDD domain), and antisense mRNA to the PLRV replicase.

Braun et. al., (1992), has shown that the expression of the amino terminal 674 amino acids or full length viral replicase for potato virus X (PVX) generates plants highly resistant to infection by PVX. Braun et. al., (1992), has also demonstrated that vectors which expressed the NTP or GDD domains separately did not produce plants resistant to PVX. A plant expression vector was designed as described in the EXAMPLE containing SEQ ID NO. 1, which includes the full length putative replicase gene (ORF 2a/2b).

Golemboski et al. (1990) has shown that expression of a truncated form of the TMV replicase gene the 54 kDa read-through protein containing the GDD motif is sufficient to cause resistance against the homologous TMV strain. Although Braun et. al., (1992), reported that the GDD domain for PVX was not sufficient to cause resistance to PVX infection, this phenomenon of GDD-mediated resistance may be virus specific. Therefore, based on the discovery by Golemboski et al. (1990), a construct was designed (as described in the EXAMPLE) which contains the GDD domain.

Because the replicase is an important component in the PLRV infection cycle and is the largest ORF in the PLRV genome, the approach was taken to express antisense mRNA, as described in the EXAMPLE, for the putative replicase gene (ORF2a/2b). One rationale for over-expressing antisense or minus strand message as a transgene is to competitively bind invading PLRV genomic positive strand RNA, therefore blocking translation of the PLRV replicase gene, and providing a mechanism of resistance against PLRV.

SEQ ID NO. 1 contains the PLRV replicase cDNA which is the source of the nucleotide sequence used in this described invention. The nucleotide sequence of the replicase gene may be modified, for example, at the 5' and 3' ends to facilitate cloning. Additional modifications may be performed to eliminate the natural frameshifting mechanism by inserting, removing, or changing certain nucleotides such that the full length 110 kDa replicase protein is produced at frequencies greater than 1% as previously described. This may be accomplished by site-directed mutagenesis, using methods known to those skilled in the art, and may provide different restriction sites as needed. Various oligonucleotide primers may be used to modify the 5' end to include a better context surrounding the translation initiation codon (ATG). In plants it has been shown that the optimal context surrounding the ATG is guanine or cytosine at −5, followed by two adenines, followed by any two nucleotides followed by the translation initiation codon (ATG) followed by guanine at +4 [(G/C A A N N ATG G) (Lutcke et.al., 1987)]. The 3' end of the gene can also be modified for a plant-preferred termination codon (TAA) (Murray et. al., 1989). Alternatively, the engineered gene can be constructed in such a way as to contain a preferred amino acid codon usage for the target organism in which the gene is to be expressed (Perlak et. al., 1991).

Sequencing of the replicase gene was performed by the method of Sanger et. al., (1977) using the Sequenase® polymerase, according to United States Biochemical's recomendations. The nucleotide sequence was used to predict the amino acid sequence of the gene product. In this and all predicted amino acid sequences herein, the standard single letter nomenclature is used. All peptide sequences represented here are shown in conventional format wherein the N-terminus appears at the left and the C-terminus at the right.

It is understood that the particular nucleotide and/or amino acid sequences disclosed in the FIGUREs are representative in the sense that equivalent genes or portions thereof may be obtained and/or generated pursuant to this disclosure. By equivalent it is meant that said gene or portion thereof would function in a manner substantially the same as the replicase gene disclosed herein, and would provide viral resistance to a plant in substantially the same manner.

The PLRV replicase cDNA sequence (SEQ ID NO. 1) may be inserted into a plant expression vector, such as pMON18608 (FIG. 2), as a gene capable of being expressed in a plant. A plant expression vector contains the necessary elements to stably integrate a gene to be expressed in plants and passed on to its progeny. A gene is defined as an element or combination of elements that are capable of being expressed in a cell, either alone or in combination with other elements. In general, a gene comprises (from the 5' to the 3' end): (1) a promoter region which includes a 5' non-translated leader sequence capable of functioning in plant cells; (2) a gene or DNA sequence which codes for the desired protein; and (3) a 3' non-translated region, which typically causes the termination of transcription and the polyadenylation of the 3' region of the RNA sequence. Each of these elements is operably linked by the sequential attachment to the adjacent element. A gene comprising the above elements may be inserted by standard recombinant DNA methods into a plant expression vector. Some or all of the elements of the gene may be present, with additional or remaining elements added to the vector if necessary. A further aspect of the present invention is the introduction of multiple copies of the replicase gene into the plant genome. Additionally, the plant expression vector may be constructed with all of the elements present except for the gene, an Example is pMON18608 (FIG. 2), the gene may then be added at an appropriate time by methods known to those skilled in the art.

The segment of DNA referred to as the promoter is responsible for the regulation of the transcription of DNA into mRNA. A number of promoters which function in plant cells are known in the art, and may be employed in the practice of the present invention. These promoters may be obtained from a variety of sources such as plants or plant viruses, and may include but are not limited to promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. Other useful promoters include promoters which are capable of transcribing the replicase gene in an inducible manner or in a tissue-specific manner in certain cell types in which the infection is known to occur. For Example, the promoters from the genes of any of the following inducible proteins: phenylalanine ammonia lyase, chalcone synthase, hydroxyproline rich glycoprotein, extensin, pathogenesis-related proteins (e.g. PR-1a), and wound-inducible protease inhibitor from potato would be useful.

Alternate promoters, such as the glutamine synthetase promoter could be used to express the protein in certain cell types, such as phloem cells. The patatin promoter could be used to express the protein in the potato tuber. The particular promoter selected is preferably capable of causing sufficient expression of the replicase gene to which it is operably linked, resulting in the production of an effective amount of the replicase protein to provide viral resistance, but not so much as to be detrimental or lethal to the plant cell in which it is expressed. The promoters selected should be capable of functioning in tissues including but not limited to epidermal, vascular, and mesophyll tissues. The actual choice of the promoter should provide sufficient transcriptional activity to accomplish the expression of the replicase gene and subsequently confer viral resistance in plants.

The non-translated leader sequence can be derived from any suitable source and can be specifically modified to increase the translation of the mRNA. The 5' non-translated region can be obtained from the promoter selected to express the gene, the native leader sequence of the gene or coding region to be expressed, viral RNAs, suitable eucaryotic genes, or a synthetic gene sequence. The present invention is not limited to the construct presented in the following EXAMPLE.

The termination region or 3' non-translated region is employed to cause the termination of transcription and the addition of polyadenylated ribonucleotides to the 3' end of the transcribed mRNA sequence. The termination region may be native with the promoter region, native with the gene, or may be derived from another source, and would preferably include a terminator and a sequence coding for polyadenylation. Suitable 3' non-translated regions of the chimeric plant gene include but are not limited to: (1) the 3' transcribed, non-translated regions containing the polyadenylation signal of Agrobacterium tumor-inducing (Ti) plasmid genes, such as the nopaline synthase (NOS) gene, and (2) plant genes like the soybean 7S storage protein genes and the pea small subunit of the ribulose 1,5-bisphosphate carboxylase-oxygenase (ssRUBISCO gene), which is referred to hereinafter as E9.

In developing the expression construct, the various components of the expression construct or fragments thereof will normally be inserted into a convenient cloning vector, which is capable of replication in a bacterial host, such as *E. coli*. Numerous vectors exist that have been described in the literature. After each cloning, the vector may be isolated and subjected to further manipulation, such as restriction endonuclease digestion, insertion of new fragments, ligation, deletion, insertion, in vitro mutagenesis, addition of polylinker fragments, and the like, in order to provide a vector which will meet a particular need. Once the construct is completed, it may then be transferred to an appropriate vector for further manipulation in accordance with the manner of transformation of the plant cell and expression of a foreign gene in the plant cell.

A variety of techniques are available for the introduction of the genetic material into or transformation of the plant cell genome. However, the particular manner of introduction of the plant vector into the host is not critical to the practice of the present invention. Any method which provides for efficient transformation may be employed. In addition to transformation using plant expression vectors derived from the tumor-inducing (Ti) or root-inducing (Ri) plasmids of Agrobacterium, alternative methods could be used to insert the DNA constructs of the present invention into plant cells. Such methods may include, for example, the use of liposomes, electroporation, chemicals that increase the free uptake of DNA, DNA delivery via microprojectile bombardment, microinjection, and transformation using viruses or pollen.

A plant expression vector preferably includes all of the necessary elements for transformation of plant cells. Typical plant cloning vectors comprise selectable marker genes, scoreable marker genes, T-DNA borders, cloning sites, appropriate bacterial genes to facilitate the identification of transformants, broad host range replication and mobilization functions, and other elements as desired. The replicase gene can be inserted into any suitable plant expression vector for transformation into the desired plant species. Suitable plant expression vectors include those derived from a Ti plasmid of *Agrobacterium tumefaciens*, in addition to those disclosed, for example, by Herrera-Estrella et. al., (1983), Bevan et. al., (1984), Klee et. al., (1985) and Fraley (1983).

Selectable marker genes may be used to select for those plant cells which are transformed. Conveniently, the marker gene employed codes for resistance to an antibiotic, such as kanamycin, G418, hygromycin, streptomycin, and the like. Other markers could be employed in addition to or in the alternative, such as, for example, a gene coding for herbicide tolerance such as tolerance to glyphosate, sulfonylurea, phosphinothricin, or bromoxynil. Additional means of selection could also be employed. The particular marker employed will be one which will allow for the selection of transformed cells as opposed to those cells which were not transformed. Depending on the number of different host species one or more markers may be employed, where different conditions of selection would be used to select the different host, and would be known to those of skill in the art.

Plant expression vectors containing the potato leafroll virus replicase gene may be used to transform plants of the Solanaceae family. In particular, infection by potato leafroll virus is a persistent problem in potato and can infect tomato, peppers, and tobacco. An Agrobacterium-mediated transformation protocol is known to be effective in transforming members of the Solanaceae family. When an Agrobacterium-mediated transformation is used, the desired expression vector is mobilized into a suitable Agrobacterium strain. The ABI Agrobacterium strain is described for exemplary purposes. The desired expression vector is mobilized into an ABI::Agrobacterium strain by the triparental mating system using the helper plasmid pRK2013 (Ditta et. al., 1980). The binary ABI strain is the chloramphenicol resistant derivative of *Agrobacterium tumefaciens* A208 which carries the disarmed Ti plasmid pTiC58 (Koncz et. al., 1986). This Ti plasmid does not carry the T-DNA phytohormone genes (disarmed) and the strain is therefore unable to cause crown gall disease. The disarmed Ti plasmid provides the trfA gene functions required for autonomous replication of the vector after conjugation into the ABI strain. When the plant tissue is incubated with the ABI::expression vector conjugate, the vector is transferred to the plant cells by the vir functions encoded by the disarmed pTiC58 plasmid. The pTiC58 Ti plasmid does not transfer to the plant cells, but remains in the Agrobacterium. Either single- or double-border transformation vectors can be delivered to the plant by Agrobacterium. Single border vectors open at the right T-DNA border region, and the entire vector sequence is inserted into the host plant chromosome. The right border is lost during transfer and integration. In a double border vector, DNA between the right and left borders is inserted into the plant chromosome, thereby delivering only the chimeric genes of interest to the chromosome. The remainder of the vector, and the border sequences are lost during the transfer and integration.

Transformation and regeneration protocols for members of the Solanaceae family are known. In particular, various transformation and regeneration protocols for potato and tomato have been established. An exemplary protocol for potato is described in the EXAMPLE. After the potato plant has been transformed and after transformed callus has been identified, the transformed callus tissue is regenerated into whole plants. Any known method of regeneration of potato plants can be used in this invention.

A plant of the present invention containing the desired replicase gene is cultivated using methods known to those of skill in the art. A transformed plant of the present invention thus is capable of expressing the replicase gene and exhibits viral resistance thereby. The presence of the replicase gene, or gene product, in the transformed plant may be determined by any suitable method known to those skilled in the art. Included in these methods are Southern, northern, and western blot techniques, ELISA, and bioassays. The transformed plant capable of expressing replicase may then be assayed for the determination of resistance effectiveness. A representative assay to accomplish this is included in the EXAMPLE.

The following EXAMPLE is provided to elucidate better the practice of the present invention and should not be interpreted in any way as to limit the scope of the present invention. Those skilled in the art will recognize that various modifications can be made to the methods and genes described herein while not departing from the spirit and scope of the present invention. For the sake of clarity and brevity of explanation, the following description of the particular embodiments will be exemplified by the use of potato leafroll virus (PLRV) replicase gene and resistance in transgenic Russet Burbank potato plants.

EXAMPLE

General information pertinent to the EXAMPLE:

Strains and Plasmids

Figure 6:
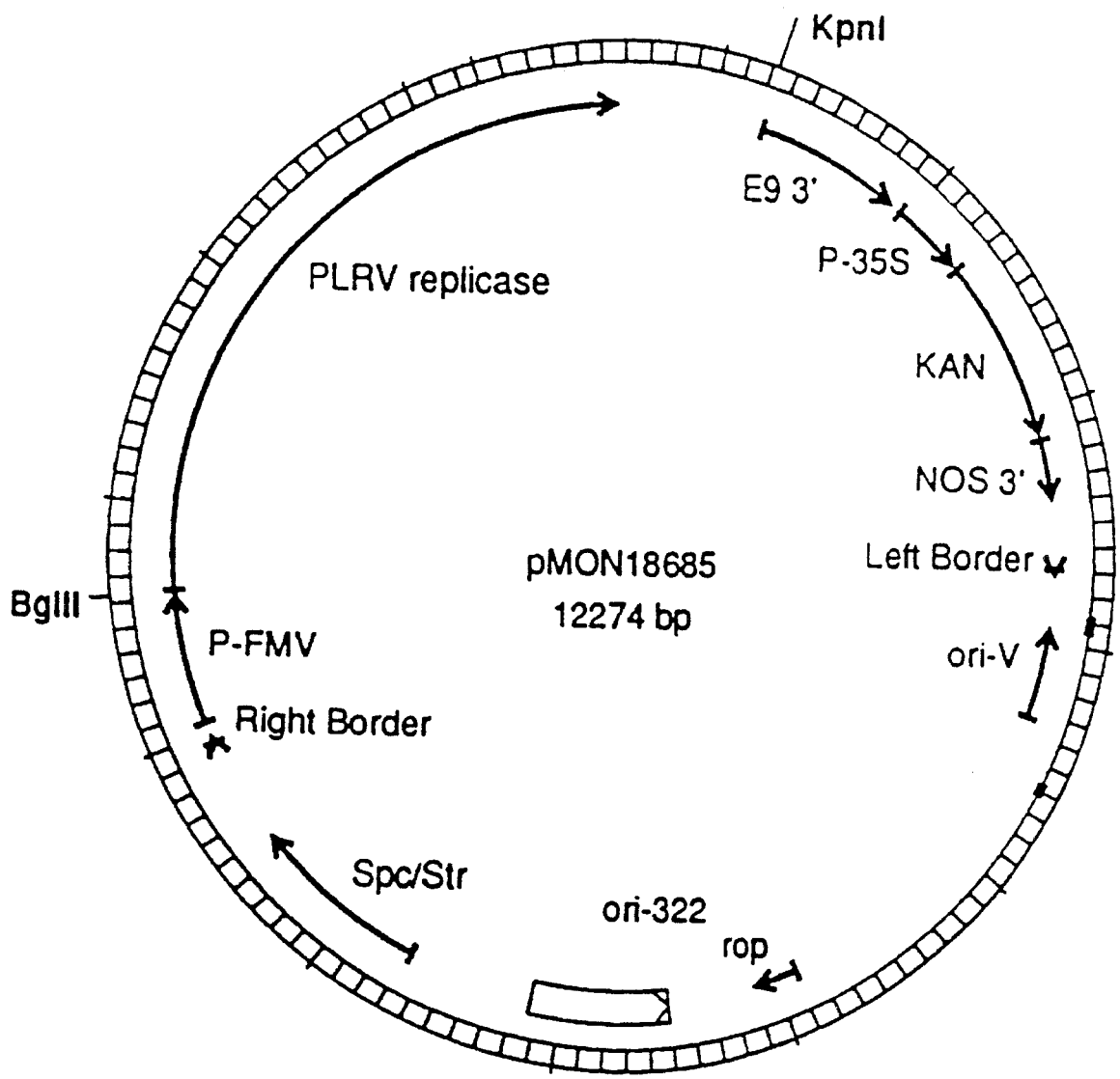
FIG. 6 illustrates a physical map of the plasmid pMON18685.
Figure 7:
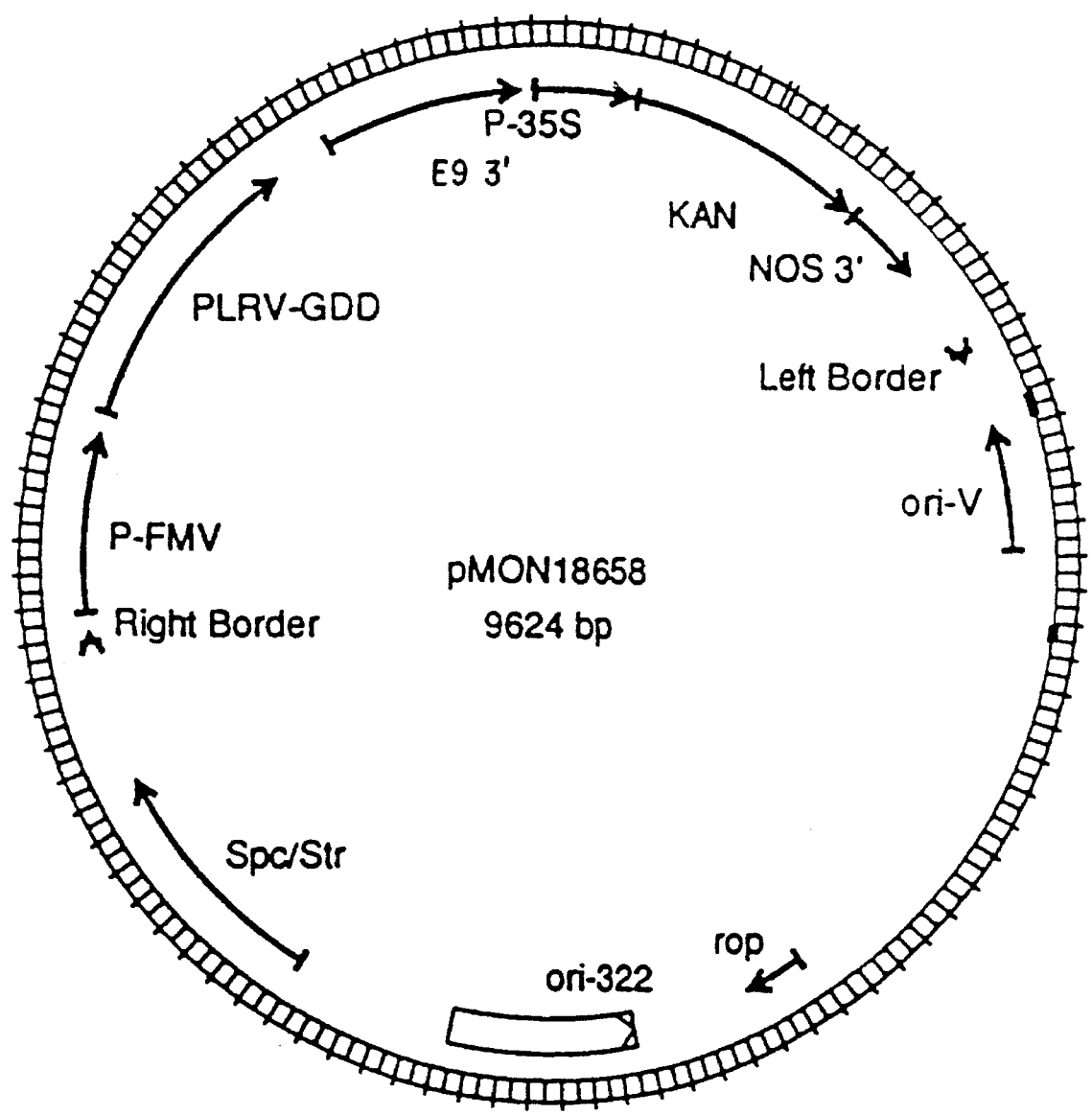
FIG. 7 illustrates a physical map of the plasmid pMON18658.
Figure 8:
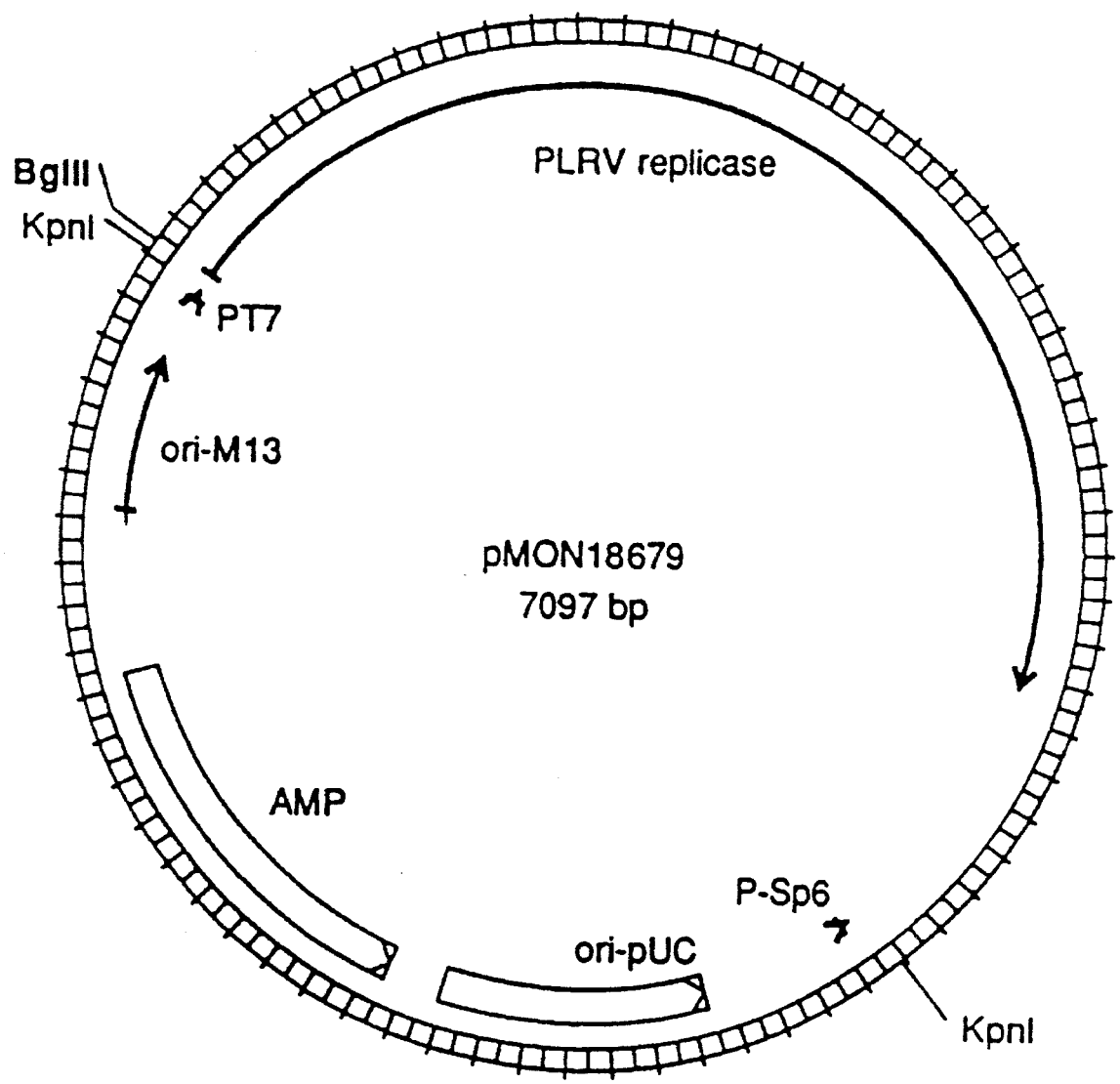
FIG. 8 illustrates a physical map of the plasmid pMON18679.

E. coli strain MV 1190 (from BioRad)
Agrobacterium strain ABI
helper plasmid pRK20 13
pMON18608 (FIG. 2)
pMON8574 (FIG. 3)
pMON18643 (FIG. 4)
pMON18644 (FIG. 5)
pMON18685 (FIG. 6)
pMON18658 (FIG. 7)
pMON18679 (FIG. 8)

Enzymes and Kits

DNA sequencing kit:
Sequenase v2.0 Sequencing Kit United States Biochemical #70770
In vitro mutagenesis kit:
BioRad Mut-a-gene in vitro mutagenesis kit #170–3578

MODIFYING ENZYMES

Alkaline Phosphatase from calf intestine (CIP):
Boehringer Mannheim #713023

RESTRICTION ENZYMES

The following are restriction enzymes with recognition sequence designated in a 5' to 3' direction and used according to the recommendations of New England Biolabs:
EcoRI (G↓AATTC) from New England Biolabs CAT#101
Kpn I (GGTAC↓C) from New England Biolabs CAT#142
STu I (AGG↓CCT) from New England Biolabs CAT#187
BsaAI (YAC↓GTR) from New England Biolabs CAT#531
Bgl II (A↓GATCT) from New England Biolabs CAT#144

Media and Solutions

LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0.

MSO contains 4.4 g MX salts (Sigma Chemical Co., St. Louis, Mo.), 30 g sucrose and 2 ml $B_5$ vitamin (500X) in a 1 liter volume, pH 5.7.

PM media contains 4.4 g MS salts (Sigma Chemical Co., St. Louis, Mo.), 30 g sucrose, 0.17 g $NaH_2PO_4.H_2O$, 1 ml thiamine HCl and 0.1 g inositol in a 1 liter volume, pH 6.0 and 0.2% Gelrite agar.

callus induction media contains 5.0 mg/l Zeatin Riboside, 10 mg/l $AgNO_3$, and 0.1 mg/l NAA.

shoot induction media contains MSO plus 5.0 mg/l Zeatin Riboside, 10 mg/l $AgNO_3$ and 0.3 mg/l $GA_3$ (gibberellic acid) and 100 mg/l kanamycin.

NAA is naphthaleneacetic acid.

LB media contains 10 g tryptone, 5 g yeast extract and 5 g NaCl per liter pH7.0.

PBS-T-O contains 8 g NaCl, 0.2 g $KH_2PO_4$, 2.9 g $Na_2HPO_4.12\ H_2O$, 0.2 g KCl, 0.05% Tween 20, and 0.2% Ovalbumin.

PBS-T contains phosphate buffered saline as above and 0.05% Tween 20.

Unless otherwise specified, the above solutions represent the basic (1x) concentration employed. Throughout the EXAMPLE, where different concentration levels are employed, that fact is indicated by referring to the solution as a multiple of the basic (1x) concentration.

Construction of the Potato Leafroll Virus cDNA Library

Potato leafroll virus virions were purified from *Datura stramonium cv. tatula* by grinding fresh infected leaves in a Waring blender with 2 volumes of (w/v) 0.1M citrate buffer pH 6, 0.01M EDTA, 0.3% (w/v) DIECA (diethylthiocarbamic acid, sodium salt, Sigma D-3506), 0.5% (v/v) 2-mercaptoethanol, and 1.5% (w/tissue wt) Rohament®. This mixture was stirred at room temperature for a minimum of 2.5 hrs, at which time 1% Triton X-100 (v/v) was added and then stirred overnight. To this was then added 20% (v/v) butanol:chloroform (1:1), which was mixed in a blender for 30 seconds and centrifuged at 6000 rpm in a Beckman JA-10 rotor for 10 minutes at 15° C. The upper aqueous phase was retained. Solid PEG 8000 8% (w/v) and 1% (w/v) NaCl was added and then stirred for 30 minutes. This was incubated at room temperature for i hour, then centrifuged at 5000 rpm for 20 minutes in JA-10 rotor at 15° C. The pellets were saved and resuspended in ¼ volume of original tissue weight (wt) of 0.1M citrate buffer pH 6.4 containing0.01M EDTA, stirred overnight at room temperature, and then clarified by centrifugation at 8000 rpm in a JA-21 rotor for 10 minutes. The supernatant was retained and then centrifuged at 30K rpm for 2 hours at 15° C. in a 45Ti Beckman rotor. The pellet was resuspended in 1/100th volume of original tissue wt in 50 mM citrate pH 6.4, and 5mM EDTA. This was stirred for 2 hours, and then centrifuged at 8000 rpm for 10 minutes at 15° C. The supernatant was retained. This was purified on a sucrose density gradient (10–40% w/v) by centrifugation for 2 hours at 25K rpm 15° C. in a Beckman SW-28 rotor. The virus band was recovered with a syringe and hypodermic needle or gradient fractionation.

PLRV RNA was extracted by incubating ≈55 μg of virus in 2.1 mls of 0.05M citrate buffer, pH 6.4, with 200 μl of 100 mM Tris pH 7.5, 200 µl of 10% SDS and 400 µl of 1 mg/ml protease K at 37° C. for 30 minutes and extracting twice with phenol and phenol chloroform (1:1 v/v), respectively. PLRV cDNA was then synthesized using random primers and the lambda gt11 (λgt11) kit according to Amersham's instructions.

A full-length PLRV replicase clone was isolated from the cDNA library, which was constructed in λgt11 using adaptors provided by Amersham cDNA cloning system. The Amersham EcoRI adaptor consists of the following:

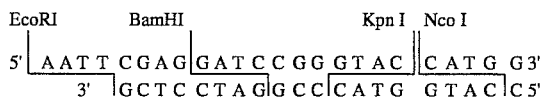

This adaptor has from 5' to 3' an EcoRI compatable overhang, BamHI, Kpn I and Nco I sites. This library was screened using an oligonucleotide primer complementary to the 5' end of ORF 2a. The sequence of the primer for screening the cDNA library for the putative replicase component is as follows:

5'GGAGGTGCCTCGGAAGTTGAAGGCCGG3'      (SEQ ID NO. 2)

This primer hybridizes to nts 122–148 of SEQ ID NO. 1.

Description of the cDNA Clone

A 3,901 nt Kpn I cDNA clone (SEQ ID NO. 1) was isolated from λgt11. This cDNA clone was mapped and sequenced to confirm the presence of a full length cDNA for the putative replicase gene (nt 41–3,225 SEQ ID NO. 1). Also present within the 3,901 nt cDNA are 40 nucleotides (nts) 5' to the translational start (ATG) of the putative replicase gene. The 40 nucleotides contain the Kpn I and Nco I restriction sites from the EcoRI adaptor and 30 nucleotides of authentic PLRV cDNA. Following the replicase termination codon (TGA) there are 666 nucleotides 3' to the putative replicase gene. Within this region there exists a 166 nt intergenic region (nt 3,226–3,422 SEQ ID NO. 1) between ORF2b and ORF 3, 468 nt from the coding region of the coat protein ORF 3, (nt 3,423–3,890 SEQ ID NO. 1) and 444 nt from the coding region of ORF 4 (nt 3,448–3,891 SEQ ID NO. 1) which may encode a putative 17 kDa nucleic acid binding protein. However, the open reading frames for the coat protein and 17 kDa protein are incomplete. The coat protein ORF is missing 52 codons, (156 nts) from the 3' end of the gene, and the 17 kDa ORF is missing 8 codons, (24 nts) from the 3' end of the gene. Because the coat protein ORF and the 17 kDa ORF are truncated, the ORFs for the coat protein and 17 kDa protein continue into the adjacent polylinker and remain open into the downstream sequence of the vector.

Construction of pMON8574

Figure 3:
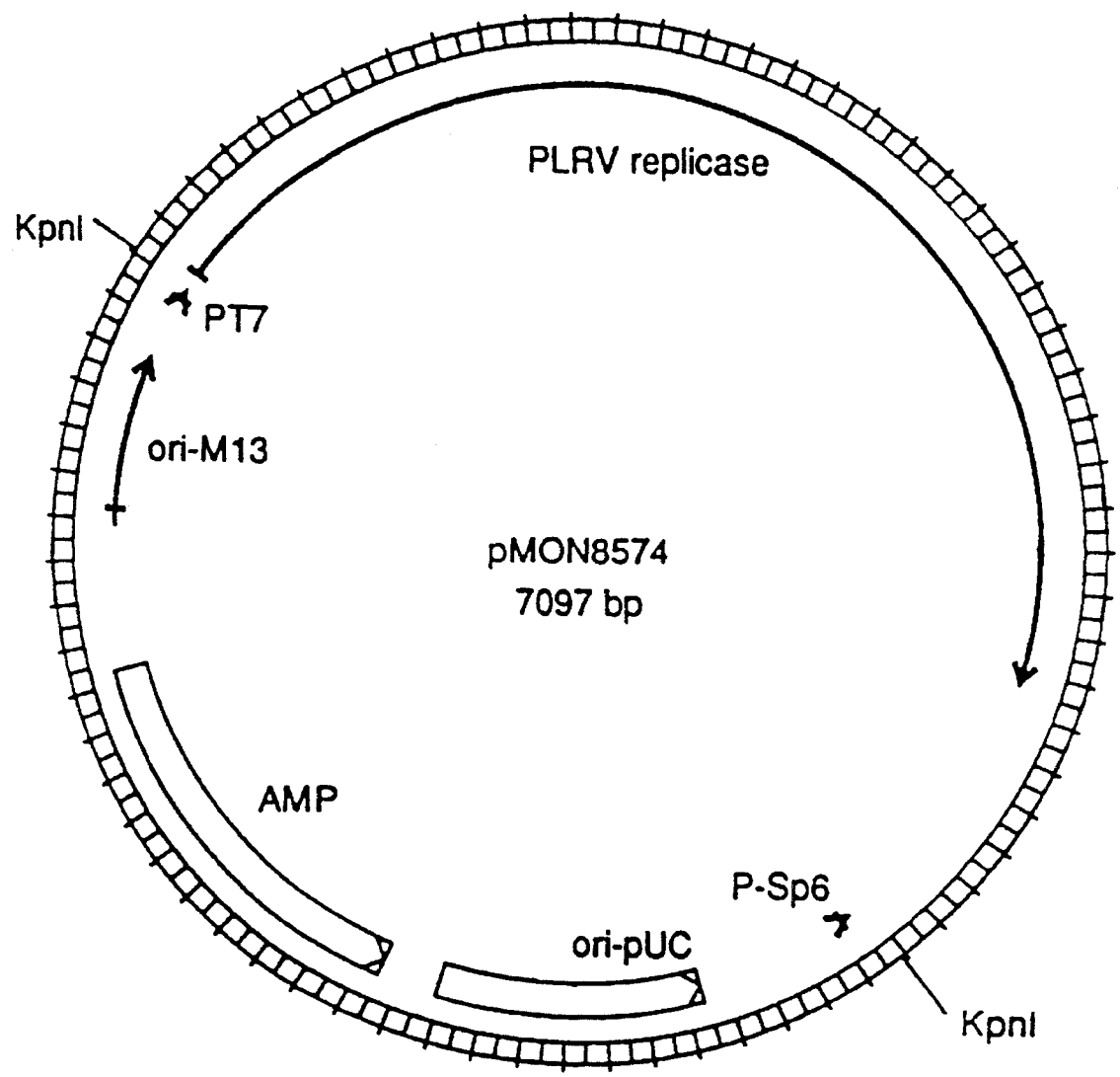
FIG. 3 illustrates a physical map of the plasmid pMON8574.
Figure 4:
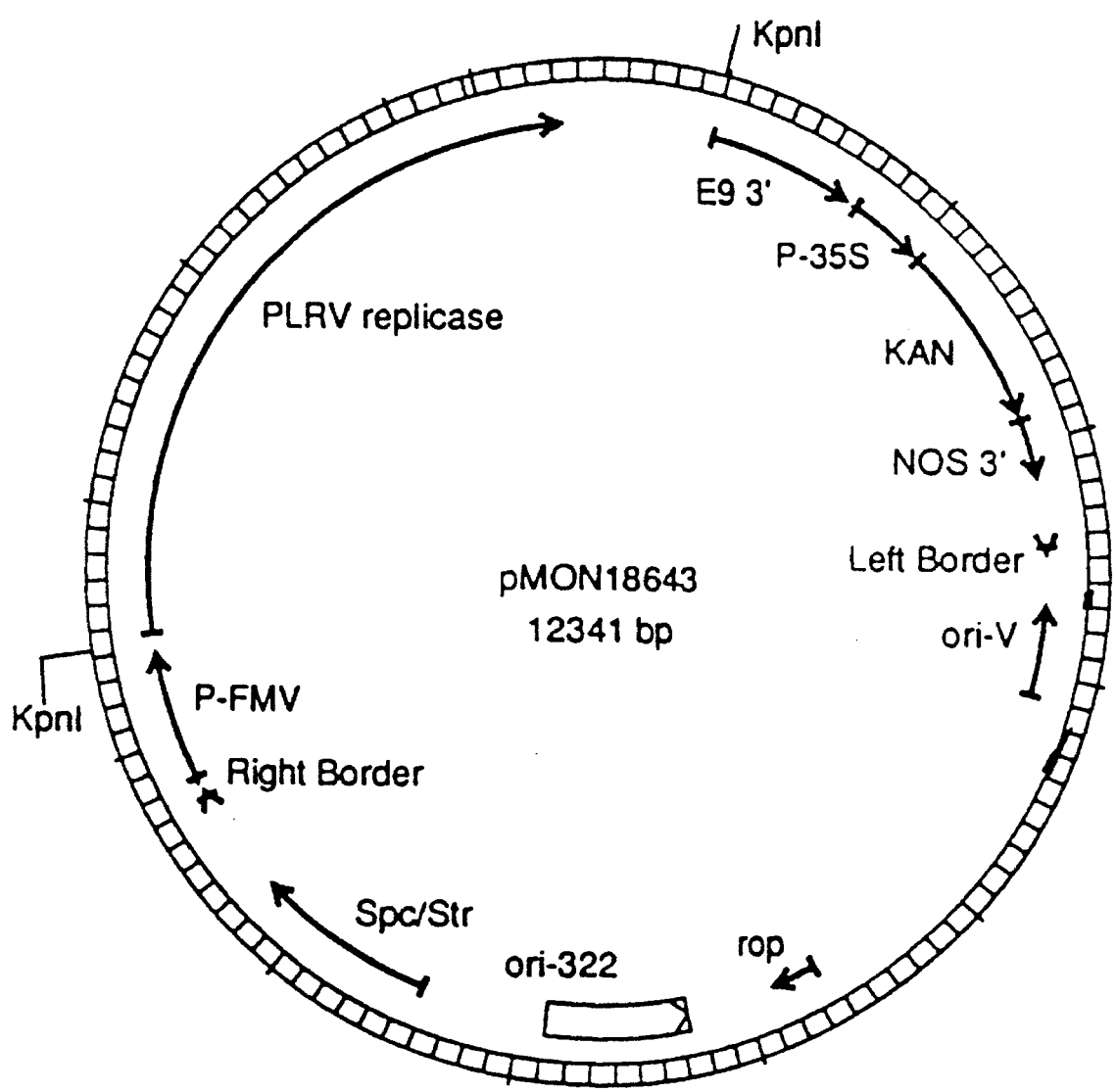
FIG. 4 illustrates a physical map of the plasmid pMON18643.

The cDNA sequence containing the putative replicase gene and downstream sequence was digested with KpnI. The 3,901 nt Kpn I fragment was cloned into pGEM 3Zf(-) (source: Promega Corp., Madison, Wis.) which was pretreated by Kpn I digestion and calf intestinal alkaline phosphatase (CP) digestion according to the manufacturer's recomendations. A clone was identified and designated pMON8574 (FIG. 3). This clone was orientated such that replicase RNA (sense-strand) could be transcribed using the T7 bacteriophage transcriptional promoter.

Description of pMON18608 Plant Transformation Vector

The plasmid pMON18608 (FIG. 2) is the plant expression vector used in this EXAMPLE, which is designed with a multiple cloning site, and was used to clone DNA fragments or genes capable of conferring PLRV resistance as described herein. pMON18608 contains no genes within the vector which are capable of conferring resistance to PLRV.

Figure 2:
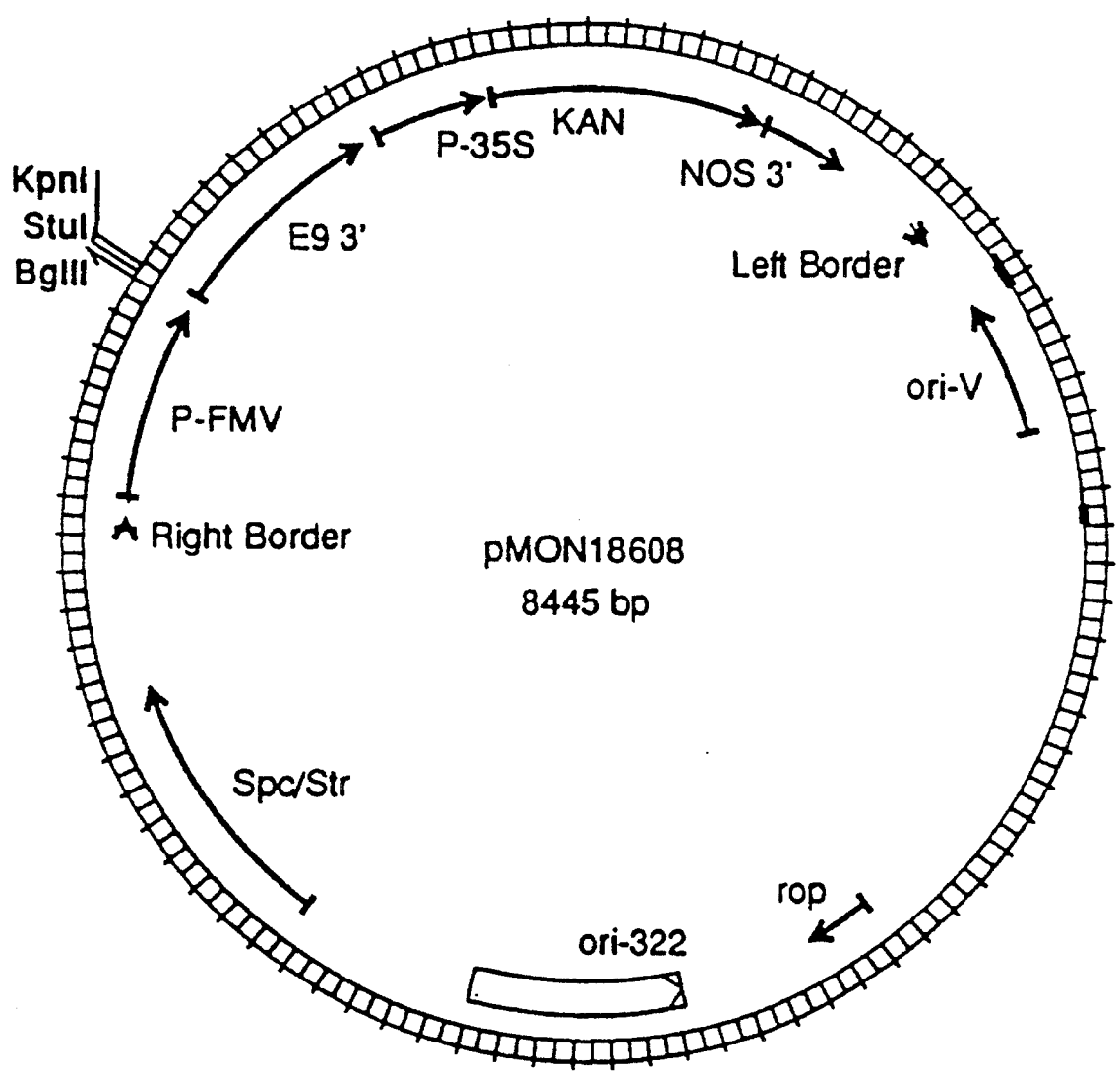
FIG. 2 illustrates a physical map of the plasmid pMON18608.

Plasmid pMON18608 contains the following DNA segments. Starting near the bottom of FIG. 2 is the origin of bacterial replication for maintenance in E. coli (ori-322) and includes the bom site for conjugational transfer into Agrobacterium tumefaciens cells. Moving in a counter-clockwise direction following ori-322 is rop, also referred to as rom, which is the coding sequence for repression of primer. Continuing in a counter-clockwise direction is the ori-V, which is the vegetative origin of replication (Stalker et al. 1981), which is then followed by the left border sequence where T-DNA insertion into the plant genome is terminated. This is followed by the chimeric gene used as the selectable marker. The chimera includes 0.35 kilobase (kb) of cauliflower mosaic virus 35S promoter (p-35S) (Odell et. al., 1985), 0.83 kb neomycin phosphotransferase type II gene (KAN), and 0.25 kb 3' non-translated region from the nopaline synthase gene (NOS 3') (Fraley et. al., 1983).

Following the gene which is used as a selectable marker, there is 0.65 kb of the E9 3' region from the pea small subunit RUBISCO gene (Coruzzi et. al., 1984). The next region contains a polylinker whose Bgl II, Stu I, and Kpn I restriction sites are highlighted. This is the location where the DNA sequence capable of conferring PLRV resistance may be fused to the FMV promoter and the E9 3' region. A DNA sequence containing the FMV promoter functions as the transcriptional promoter for the DNA sequence cloned into the polylinker site. Following the FMV promoter is the right border sequence where T-DNA insertion begins integration into the plant chromosome. Next is the 0.93 kb fragment isolated from transposon Tn7 that encodes the bacterial spectinomycin/streptomycin resistance (Spc/Str), which is a determinant for selection in E. coli and Agrobacterium tumefaciens (Fling et. al., 1985).

The following description of vector elements is the same for pMON18643 (FIG. 4), pMON18644 (FIG. 5), pMON18685 (FIG. 6), and pMON18658 (FIG. 7) with the exception of the DNA sequence inserted in the multiple cloning site.

Construction of pMON 18643 and pMON18644

Figure 5:
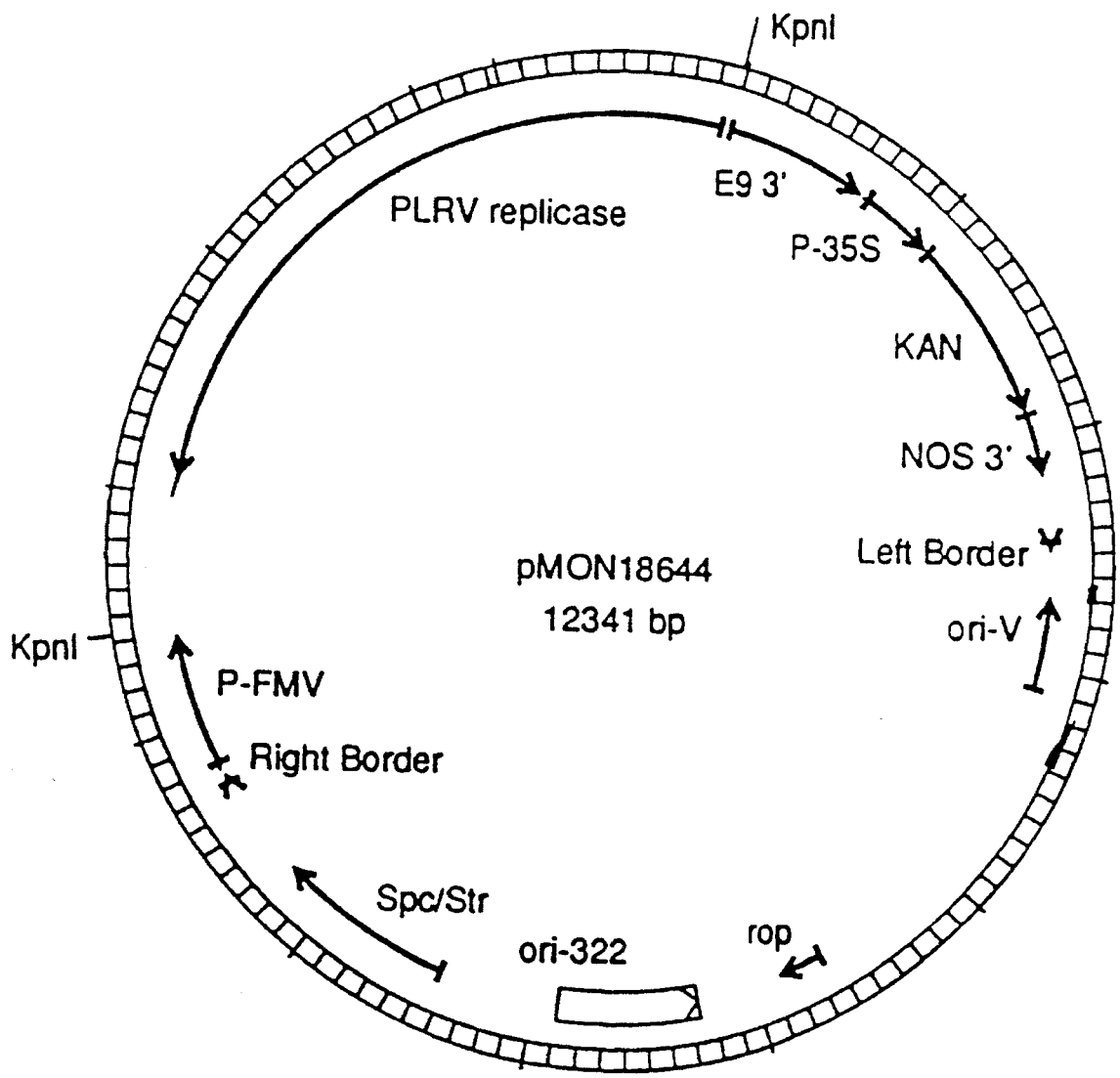
FIG. 5 illustrates a physical map of the plasmid pMON18644.

The Kpn I fragment from pMON8574 (SEQ ID NO. 1) was the source of cDNA used to produce the putative replicase DNA sequences of this invention. The KpnI fragment, SEQ ID NO. 1, was cloned into Kpn I digested and CIP treated pMON18608 in sense orientation to generate pMON18643 (FIG. 4), and in antisense orientation to generate pMON18644 (FIG. 5). The sequence of the 5' untranslated region and translation initiation (ATG) of PLRV replicase in pMON18643 was as follows:

```
        Nco I
            | 7                                      41
5'  GGTA CCATGGAGCAAGCGAGCTTAATTTACGGTTATCATCATG  3'
``` authentic PLRV cDNA sequence is in bold typeface. (Base 7 on the above FIGURE corresponds to base 7 of SEQ ID NO. 1). Within the 5' sequence of the cDNA clone for pMON8574 there is a Nco I site, which contains a translational start (ATG) codon starting at nucleotide 7. This ATG within the Nco I site creates an out of frame translation with the authentic translation initiation of the putative PLRV replicase nt 41. This first translational start (ATG) is in frame with ORF1. Also included on the Kpn I fragment cloned into pMON18643 is the ORF for the putative replicase 2a/2b protein (nt 41–3,225 SEQ ID NO. 1), an intergenic region (nt 3,226–3,422 SEQ ID NO. 1), a portion of the coat protein ORF (nt 3,423–3,890 SEQ ID NO. 1), and a portion of the ORF which codes for the putative 17 kDa nucleic acid binding protein (nt 3,448–3,891 SEQ ID NO. 1). Because the ORF for the coat protein and 17 kDa nucleic acid binding protein are truncated at the 3' end, they do not contain termination codons, therefore protein synthesis will continue into the E9 of pMON18643. SEQ ID NO. 4 contains the sequence from the 3' Kpn I site (nt 3,896–3,901 SEQ ID NO. 1) until the first in frame termination codons for the coat protein and 17 kDa ORF are found. The first in frame stop for the 17 kDa protein is at nucleotide 154 of SEQ ID NO. 4 and at nucleotide 195 of SEQ ID NO. 4 for the coat protein ORF. pMON18643 was transformed into the Russet Burbank variety of potato to test its ability to confer resistance to PLRV.

pMON18644, which drives the expression of antisense RNA, does not contain any ORF greater than 110 amino acids. The rationale for making the antisense construct was to make minus-strand RNA that would bind to the invading PLRV positive sense message, and therefore block translation of the PLRV genome during the early events of PLRV infection. pMON18644 was also transformed into Russet Burbank potato to test its ability to confer resistance to PLRV.

Construction of pMON18679

In order to create a vector which would improve the expression of the putative replicase gene (ORF 2a/2b), a Bgl II (A↓GATCT) restriction site was inserted by site-directed mutagenesis between the first ATG (nt 7 of SEQ ID NO. 1) and the second ATG (nt 41 of SEQ ID NO. 1)which encodes ORF 2a/2b. The oligonucleotide used to perform the mutagenesis according to the Mut-a-Gene® procedure described by Bio-Rad was:

5'-TCTGTTCATGATAGATCTCGTAAATTAAGCTC-3'  (SEQ ID NO. 3)

The resulting mutation inserted a BglII site nine nucleotides upstream of the translational start (AUG) for PLRV replicase and was named pMON18679. This vector is a derivative of pMON8574.

```
  Bgl II
      |                 41
    A GATC  TATCATG
    TCTAG  ATAGTAC
```

Construction of pMON 18685

The DNA coding sequence, as a Bgl II-Kpn I fragment from pMON18679 coding for the PLRV replicase gene, was engineered into pMON18608 (FIG. 2) to study its ability to confer resistance to PLRV in Russet Burbank expressing the replicase RNA and protein or proteins. The resulting vector, pMON18685 (FIG. 6) contains nt 38–3,901 of SEQ ID NO. 1. Within the sequence is 5 nt from the Bgl II insertion, 3 nt of 5' untranslated authentic PLRV cDNA, the coding sequence for ORF 2a and ORF 2b and 666 nt of 3' authentic PLRV cDNA. Present within the 666 nucleotides of 3' sequence is an intergenic region (nt 3,226–3,422 SEQ ID NO. 1), a portion of the coat protein ORF (nt 3,423–3,890 SEQ ID NO. 1) and a portion of the putative 17 kDa nucleic acid binding protein ORF (nt 3,448–3,891 SEQ ID NO. 1). Because the coat protein and 17 kDa nucleic acid binding protein ORFs are truncated at the 3' ends, they do not contain a termination codon. Protein synthesis from mRNA produced from these genes will continue into the E9 3' region of pMON18685. SEQ ID NO. 4 contains the sequence from the 3' Kpn I site (nt 3,896–3,901 SEQ ID NO. 1) until the first in frame termination codons for the coat protein and 17 kDa ORF are found. The first in frame stop for the 17 kDa protein is at nucleotide 154 of SEQ ID NO. 4. and at nucleotide 195 of SEQ ID NO. 4 for the coat protein ORF. pMON18685 was transformed into the Russet Burbank variety of potato to test its ability to confer resistance to PLRV.

Construction of pMON18658

A truncated replicase construct containing the GDD motif was constructed from SEQ ID NO. 1. A plant expression vector coding for 51% (nt 2,275–3,222 SEQ ID NO. 1) of the PLRV ORF 2b was generated using a Hind III site (A↓AGCTT) (nt 2,227–2,232 SEQ ID NO. 1), filled in with Klenow and dNTP's to remove 5' overhang, and a unique Bsa AI site (CAC↓GTG) (nt 3,404–3,409 SEQ ID NO. 1). The 1,178 nt fragment contains 47 nt (nt 2,228–2,274 SEQ ID NO. 1) of untranslated 5' sequence, the coding sequence for the GDD domain (nt 2,275–3,222 SEQ ID NO. 1), and 181 nt (nt 3,226–3,406 SEQ ID NO. 1) of 3' untranslated sequence. A partial ORF2b of 316 codons (nt 2,275–3,222 SEQ ID NO. 1) which contains the GDD domain was generated. The described fragment was cloned in the sense orientation into pMON18608 digested with Stu I and CP.

The resulting plasmid, designated pMON18658, was transformed into the Russet Burbank variety of potato for evaluation of resistance.

Construction of Additional Vectors to Confer PLRV Resistance

Those skilled in the art will recognize variations in the design of expression constructs of SEQ ID NO. 1 for conferring PLRV resistance. Of these vectors is the preferential expression of only the 2a ORF or only the 2b ORF, or expression of both ORFs separate from each other in the same expression vector utilizing the same promoter or different promoters. Vectors could be constructed by cutting pMON18685 with Hind III in a partial digestion to utilize a Hind III site at nucleotide 2,227 of SEQ ID NO. 1. The vectors should be filled in with Klenow and dNTP's to eliminate the 5' overhang, thus creating a blunt ended cloning site. The vectors would then be cut with Bgl II and the fragment containing the 2a domain isolated. This fragment could be cloned into pMON11781 cut with Bgl II and Stu I.

Further variations of SEQ ID NO. 1's coding potential would eliminate the coding regions of the structural genes 3' to the termination codon (TGA) of the replicase construct pMON18685 (nt 3,226–3,891 SEQ ID NO. 1). A method for constructing this expression vector would be to digest pMON18685 with Bgl II and BsaAI and clone the fragment containing the PLRV replicase gene into pMON11781 digested with Bgl II and Stu I. The resulting plasmid would be named pMON18821.

Additionally, constructs could be designed to eliminate, by site directed mutagenesis or other techniques known to those skilled in the art, the natural frameshift site by inserting, removing, or changing certain nucleotides within the frameshift region of SEQ ID NO. 1 (nt 1,501–1,507). A mutagenesis primer could be used which would insert a T nucleotide after nucleotide 1,507 in SEQ ID NO. 1 and would also change nucleotides within the frameshift site, so frameshifting would no longer occur. This insertion and changes would alter the natural frame shifting site, thus expressing a full length (2a/2b) 110 kDa putative replicase gene. The mutagenesis primer for altering the frame shift site would be as follows:

SEQ ID NO. 5
5'-CGGTGCCGCTTGCCCAATTCAAGGGCTTGTTTGTTG-3'

The following is the translation of the mutated frameshift site from the mutagenesis primer shown above. The underlined amino acid sequences indicate the authentic ORF2b amino acid sequences. Highlighted in bold and underlined are the nucleotides which would have been altered in the original SEQ ID NO. 1.

```
5'  CA ACA AAC AAG CCC TTG AAT TGG GCA AGC GGC ACC G
     T   N   K   P   L   N   W   A   S   G   T
                                ─────────────────
                                       ORF2B
```

Modifications may also be made to the PLRV coding sequences of SEQ ID NO. 1 discussed herein in order to further enhance the resistance to PLRV infection. Modifications as contemplated by this disclosure would include any intentional changes in the PLRV coding sequences, and would include but is not limited to additions, deletions, substitutions, and combinations thereof. Constructs could also be designed specifically in which the NTP domain of ORF2a and/or the GDD domain of ORF2b is modified.

The resistance spectrum of expressing the PLRV replicase, or SEQ ID NO. 1, or variations in part of SEQ ID NO. 1, against non-homologous or diverse strains of PLRV is unknown. A possible mechanism to extend the resistance could be obtained by combining the replicase, or SEQ ID NO. 1, or variations in part of SEQ ID NO. 1, with the coat protein structural gene (ORF 3) or any variation of the coat protein gene or coding potential of the coat protein gene. This combination of the coat protein structural element with a non-structural replicase gene could provide a broad spectrum of resistance.

The spectrum of virus resistance could also be extended by combining replicase genes or other genes from unrelated viruses to provide resistance to both viruses. For instance, one could combine the PLRV replicase gene in an expression vector with a PVY replicase gene, or PVY coat protein gene, and obtain resistance to both PLRV and PVY. This is an example of the application which could be applied in any combination with any of the genes, structural or non-structural, that have been shown to provide resistance to any virus.

A broad spectrum of resistance may also be extended by fusion of the replicase gene with other genes, such as, for example, other PLRV replicase genes. This may be accomplished by a translational fusion of the 2a domain of one PLRV isolate with the 2b domain of a different isolate, resulting in a chimeric replicase gene. This chimeric replicase gene may provide protection to both isolates, which may not have been accomplished by expression of a non-chimeric replicase gene. Alternative fusions may also be constructed which may provide the resistance.

Expression vectors containing still further combinations of the PLRV replicase gene (SEQ ID NO. 1) and genes providing other traits could also be constructed. Examples include genes encoding insecticidal proteins, such as those derived from *Bacillus thuringiensis*, or genes providing an improved quality trait, such as those genes which relate to the production of high solids.

Triparental Mating Procedure

Prior to transformation, *E. coli* containing the pMON vectors were mated into Agrobacterium ABI by a triparental mating with the helper plasmid pRK2013 (Ditta et al. 1980). ABI is the A208 *Agrobacterium tumefaciens* strain carrying the disarmed pTiC58 plasmid pMP90RK (Koncz and Schell, 1986). The disarmed Ti plasmid provides the trfA gene functions that are required for autonomous replication of the pMON vector after the conjugation into the ABI strain. When plant tissue is incubated with the ABI::pMON conjugate, the vector is transferred to the plant cells by the vir functions encoded by the disarmed pMP90RK Ti plasmid. Agrobacteria were grown 30 hours in LB media (10 g tryptone, 5 g yeast extract and 5 g NaCl per liter) with 25 µg/ml chloramphenicol (Sigma Chemical Co.) and 50 µg/ml kanamycin (Sigma Chemical Co.) at 30° C. *E. coli* containing pRK2013 were grown overnight in kanamycin (50 µg/ml). *E. coli* containing with pMON vectors were grown in LB with 75 µg/ml spectinomycin (Sigma Chemical Co.). When the cultures were grown, 4 ml of LB was added to a tube with 100 µl each of Agrobacterium ABI, *E. coli* pRK2013, and *E. coli* pMON vector. This mixture was centrifuged for 5 minutes at 5000 × g. Following centrifugation the supernatant fraction was decanted and the pellet fraction was resuspended in 100 µl of LB. 25 µl of the respended bacteria was pipetted into the center surface of an LB plate. After overnight growth at 30° C., an inoculation loop of cells from this plate was streaked onto an LB plate supplemented with 75 µg/ml spectinomycin, 50 µg/ml kanamycin and 25 µg/ml chloramphenicol.

After 24–48 hours at 30° C., the plate from the triparental mating of a *E. coli* pMON vector, *E. coli* pRK2013 and Agrobacterium ABI contained bacteria colonies. Four of these colonies were selected from the triparental mating plate, inoculated into a liquid culture of LB supplemented with 75 µg/ml spectinomycin, 50 µg/ml kanamycin and 25 µg/ml chloramphenicol and grown at 30° C. The presence of the pMON vector was shown by Southern analysis. One of the cultures verified to contain the pMON vector was used for transformation of Russet Burbank potato variety.

Transformation of Potato

Russet Burbank potatoes were transformed with four different replicase constructs pMON18685, pMON18643, pMON18644 and pMON18658. To transform potatoes using kanamycin (Sigma Chemical Co.) as a selectable agent, Agrobacterium was grown overnight in 2 ml of LBSCK. The following day, the bacteria was diluted 1:10 with MSO or until an optical density reading of 0.2–0.33 was established. Leaves were removed from the stems of potato plants that had been grown under sterile conditions for three weeks on PM media supplemented with 25 mg/ml ascorbic acid, stems were cut into 3–5 mm segments and inoculated with diluted bacteria as described previously.

Explants were placed onto prepared co-culture plates. The co-culture plates contained $\frac{1}{10}$ MSO with 1.5 mls of TxD cells overlayed with wetted filter paper. About 50 explants were placed per plate. After a 2 day co-culture period, explants were placed onto callus induction media which contained MSO plus 5.0 mg/l Zeatin Riboside, 10 mg/l AgNO3, 0.1 mg/l NAA, and 100 mg/l kanamycin for four weeks. After 4 weeks, explants that exhibited growth in the presence of kanamycin were placed on shoot induction media which contained MSO plus 5.0 mg/l Zeatin Riboside+ 10 mg/l AgNO3 and 0.3 mg/l $GA_3$, with 100 mg/l kanamycin for further selection. Shoots began to appear at 8 weeks. The plants were then placed in sundae cups with PM media and allowed to grow for approximately 2 weeks. Plants were placed into soil, hardened off, and analyzed by recallusing to verify transformation, by assaying for the presence of Npt II which confers resistance to the plant to the antibiotic kanamycin. If the plant was positively recallused for expression of Npt II, the plant was kept for further study and maintained in tissue culture.

Potato PLRV Resistance Experiments

A. Growth chamber analysis of transgenic Russet Burbank

The evaluation of transgenic potato resistance to infection by PLRV was first conducted in growth chambers. Ten rooted cuttings were made from each transgenic line to assay for PLRV infectibility. Potato plants were grown in growth chambers at 24° C. 16 hour day, with moderate light intensity and 20° C. 8 hour night conditions. Two weeks post-transplanting the rooted cuttings from transgenic plants and control Russet Burbank were inoculated with PLRV using aphids. Aphids were maintained on PLRV infected *Physalis floridana*. Approximately 15 viruliferous aphids were transferred from Physalis to each potato plant. Aphids were allowed to feed for up to one week, then insecticide was applied to eliminate the aphids. After one month post inoculation, leaves and roots of each plant were sampled and analyzed by ELISA. Plants were considered infected if PLRV antigen (virus) was detected in the leaves or roots of infected plants. The results of this analysis are shown in Table 1 below. The columns are the construct numbers, the number of lines of each construct assayed and the number of those lines which fell into 3 infection categories. The highly resistant lines showed 0–20% PLRV infection, moderately resistant showed 21–60% and those with no resistance >60%. The results are that no lines from pMON18643 (out of frame replicase) were highly resistant to PLRV infection, 1 line of pMON18644 (anti-sense) of 21 assayed showed high level of resistance, 1 line of pMON18658 (3' portion of replicase gene) of 17 assayed showed high level of resistance and 1 line of 3 from pMON18685 showed a high level of resistance, and all of 12 tests of RB-wt controls were >60% infected. The conclusion was that the anti-sense (pMON18644), 3' portion (pMON18658) and sense (pMON18685) constructs containing PLRV replicase cDNA had the potential to generate Russet Burbank potato lines highly resistant to PLRV infection.

TABLE 1

| CONSTRUCT | # LINES | 0–20% | 21–60% | >60% |
|---|---|---|---|---|
| pMON18643 | 22 | 0 | 3 | 19 |
| pMON18644 | 21 | 1 | 6 | 14 |
| pMON18658 | 17 | 1 | 3 | 13 |
| pMON18685 | 3 | 1 | 0 | 2 |
| RB-WT CONTROL | 12 | 0 | 0 | 12 |

B. Field testing of transgenic Russet Burbank

Potato plantlets were propagated as cuttings from 10 Russet Burbank (RB) wild type lines (independent nontransgenic tissue culture regenerates), 14 vector control (VC) lines (transgenic Russet Burbank not containing PLRV cDNA), and from test contructs pMON18643 (17 lines), pMON18644 (22 lines), pMON18658 (19 lines), and pMON18685 (24 lines). The plantlets were transplanted into pots and held in a greenhouse until field planting. The field plot was a randomized, replicated trial with 20 plants of each line per row X 2 replications. This design was repeated at two test sites in the Northwest U.S.A. and are referred to as TEST SITE #1 and TEST SITE #2.

Two weeks post field planting, each plant was inoculated with 10–20 PLRV LR-7 viruliferous green peach aphids (*Myzus persicae*) by transferring a leaf with the aphids from PLRV LR-7 infected *Physalis floridana* to each potato plant. The viruliferous aphids crawl off the Physalis leaf and feed on the potato plants, thereby challenging the potato plants with PLRV infection. The potato plants were sprayed with insecticide 5 days after inoculation. Insecticide application was continued at regular intervals during the season until the plants began natural senescence ~16 weeks post planting.

C. Visual scoring of foliar symptoms

Each replicate at both test sites was scored for PLRV symptoms 6 weeks post inoculation. The scoring was performed blind, but was prone to cooperator subjective evaluation, at each test site and recorded or converted into a percentage of the plants in each replication showing identifiable PLRV foliar symptoms. The scores were averaged to generate a single value for each line and this value is represented as a dot on the Data graphs shown in FIGS. 9 and 10. Potato lines in which the data was not available or incomplete for both replications was not included on these graphs. The X-axis on these graphs is average percent PLRV infection measured as percentage of plants showing PLRV-like symptoms. The Y-axis (not illustrated on the FIGURE) is numbers of lines. The results are shown in FIG. 9 for TEST SITE #1 and FIG. 10 for TEST SITE #2.

Figure 9:
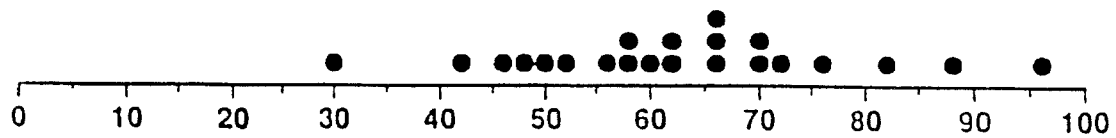
FIG. 9 illustrates the visual ratings of control and transgenic lines for PLRV symptoms at field site #1.
Figure 9:
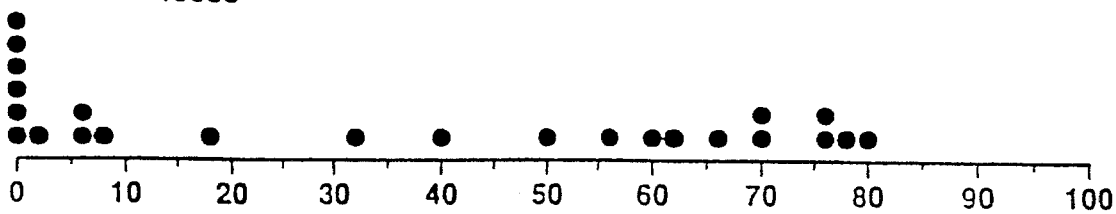
Figure 9:
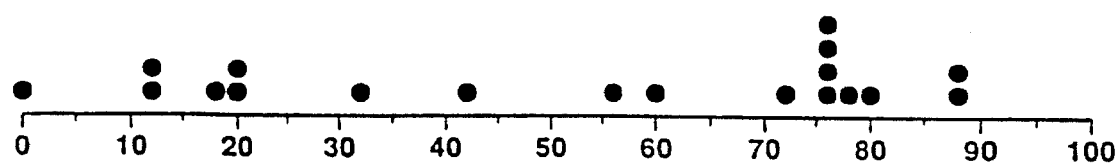
Figure 9:
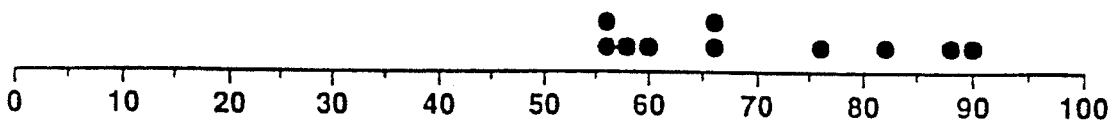
Figure 9:
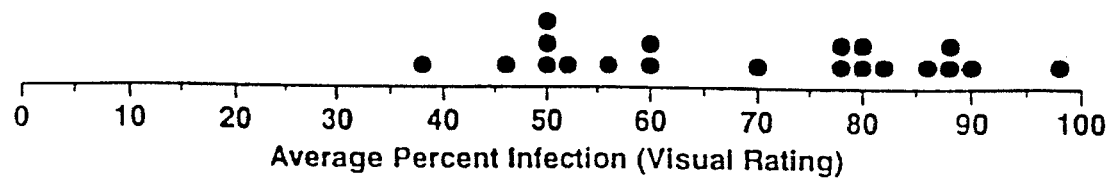

FIG. 9 shows the comparison of visual ratings of all the replicase cDNA lines with the controls in the Field Test Site #1. As can be seen in FIG. 9, 11 of 24 transgenic lines from pMON18685 (the full length PLRV replicase coding sequence), showed a high level (<20% symptoms, p=0.05) of resistance to PLRV symptoms. Six transgenic lines of pMON18658 (the 3' portion of the PLRV replicase gene), also showed significant (<20% symptoms, p=0.05) resistance to PLRV symptoms at Field Test Site #1. No lines from pMON18643 (out of frame coding sequence for PLRV replicase), showed significant reduction in PLRV symptoms. No lines from pMON18644 (anti-sense of SEQ ID NO. 1), showed significant reduction in PLRV symptoms.

Figure 10:
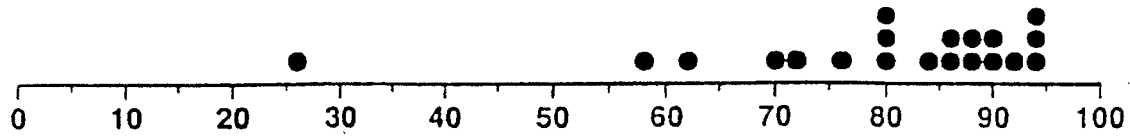
FIG. 10 illustrates the visual ratings of control and transgenic lines for PLRV symptoms at field site #2.
Figure 10:
Figure 10:
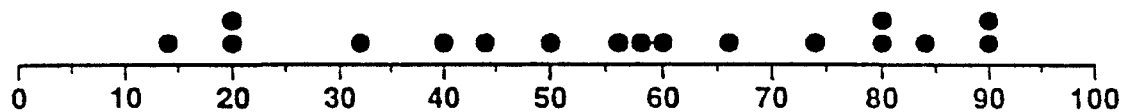
Figure 10:
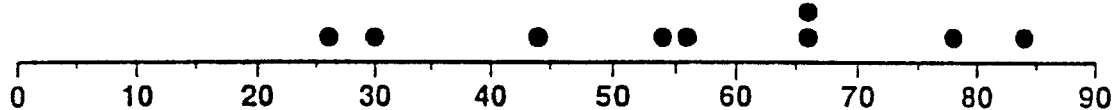
Figure 10:
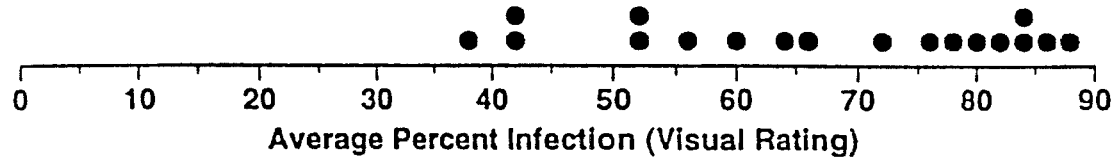
Figure 11:
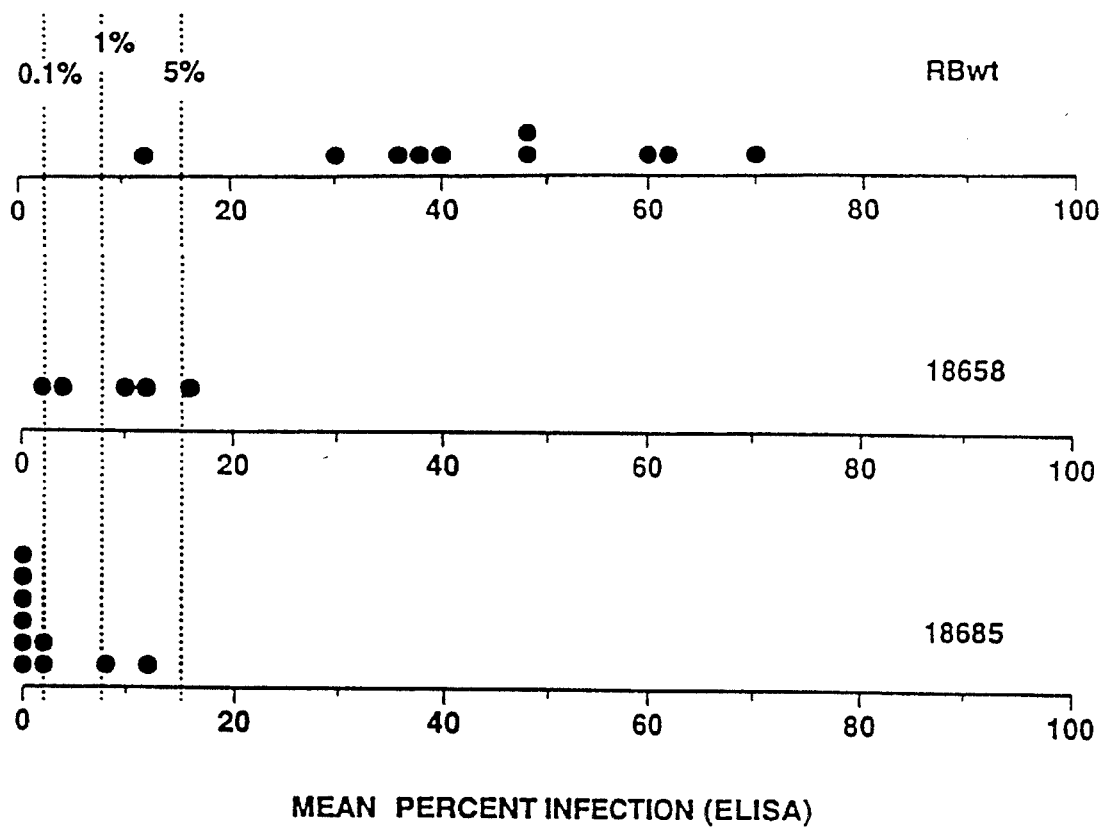
FIG. 11 illustrates the incidence of PLRV infection determined by ELISA of Russet Burbank WT control lines and transgenic lines from pMON18658 and pMON18685 at field site #1.
Figure 12:
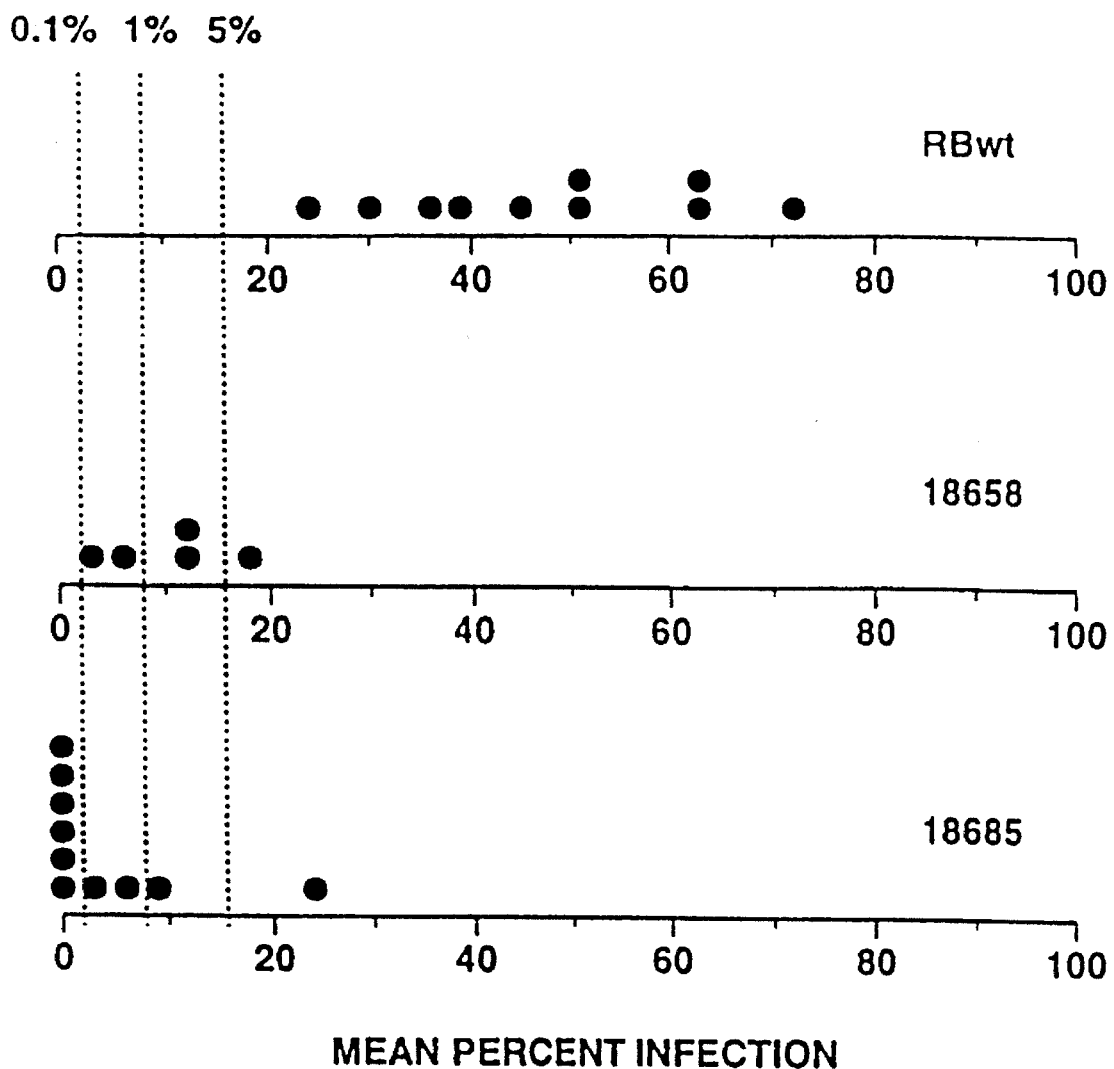
FIG. 12 illustrates the incidence of PLRV infection determined by ELISA of Russet Burbank WT control lines and transgenic lines from pMON18658 and pMON18685 at field site #2.

The results of visual observations in Field Test Site #2 are shown in FIG. 10. Four of the transgenic lines containing pMON18685 (<25% symptoms) and 3 lines of pMON18658

(<25% infection) showed resistance to PLRV symptoms. Resistance was not observed in lines transformed with pMON18643, or in plants transformed with pMON18644. The differences between the visual scores at the 2 test sites was due to subjective evaluation of symptoms by the cooperators at each site. The results from both test sites demonstrated a high level of resistance to PLRV symptoms in transgenic potato lines of pMON18658 (3' PLRV replicase coding sequence) and pMON18685 (full length PLRV replicase coding sequence).

D. ELISA analysis of PLRV

At 6 weeks post inoculation with viruliferous aphids, leaf samples were taken to assay for PLRV antigen (virus) from 10 Russet Burbank potato control lines, 5 lines of pMON18658 and 10 lines of pMON18685 transgenic Russet Burbank potato. Three leaf punches with a #6 cork borer were taken from different leaves of each plant sampled and combined as one sample for analysis. The total numbers of samples was 40 per line per test site, with all individual plants per line analyzed. The samples were shipped frozen to the lab from the 2 field sites for ELISA. The samples were homogenized with a Teflon pestle in 750 µl of PBS-T-O, and 250 µl was loaded into ELISA microtiter plates previously coated with sheep anti-PLRV IgG. The plates were incubated overnight, washed with PBS-T and incubated with sheep anti-PLRV IgG conjugated with alkaline phosphatase. Plates were incubated for 4 hrs, washed with PBS-T and developed by adding alkaline phosphatase substrate.

FIG. 11 shows a comparison of mean percent infection of lines, as determined by ELISA, of the lines sampled from pMON18685, pMON18658 and Russet Burbank wild-type (RBwt) controls at TEST SITE #1. FIG. 12 shows the same comparison of mean percent infection of lines, as determined by ELISA, from pMON18658, pMON18685 and Russet Burbank control lines at TEST SITE #2. Each dot is the mean percent infection value for the 2 replicates of each line assayed (average of 40 data points) computed as back-transformed square-root means. The statistical analysis is a 1-tailed test with percent confidence levels (0.1%, 1.0%, and 5%) indicated as vertical dotted lines. This ELISA data is more objective than visual scores. There was good correlation between the ELISA values for PLRV infection and visual observation of PLRV symptoms at both test sites. Eight lines of pMON18685 have a p=0.01 at both test sites. Two lines of pMON18658 have a p=0.01 at both test sites. Six lines of pMON18685 showed no presence of PLRV by this analysis at either of the two test sites.

E. Net Necrosis analysis of tubers from field test sites

The potatoes from the field tests of PLRV constructs were assayed for the presence of net necrosis at harvest. The net necrosis symptom in Russet Burbank potato is caused by the death of the phloem tissue in the tuber resulting in a dark discoloration which appears as a network throughout the tuber, but usually most obvious at the cut stem end of the tuber. This analysis involved cutting the stem end of tubers of each line and examining them for the net necrosis symptom. Only those tubers which clearly showed net necrosis were counted in the net necrosis category. Other tuber discolorations or defects were present at this assay point. These may be due to the presence of vascular plant pathogens such as *Verticillium spp.* and *Fusarium spp.*, or physiological factors such as heat stress, cold injury, rapid vine killing and other factors which result in a stem-end browning response. Early symptoms of PLRV-induced net necrosis may be indistinguishable from these tuber discolorations. Therefore some of the values entered in this category may develop into clearly distinguishable net necrosis after storage of the tubers. Reduction in both identifiable net necrosis and other tuber discolorations at harvest are important criteria for evaluation of PLRV resistant potato lines and selection of commercial quality plant material.

F. Net Necrosis assay procedure

All plots were harvested by rows and tubers laid on the soil surface. Tubers were scored for type from all plots. Off-type tubers were not rated for net necrosis. Eighty large tubers from selected lines from each test site (40/plot) (160 per line total) were cut for assay of the presence of net necrosis and the severity thereof. The stem end of each tuber was cut perpendicular to the long axis, then each tuber was cut in half. The tuber was rated "0" for no net necrosis or "1" for net necrosis, or was rated as a "2" if net necrosis extended to the middle of the tuber. The presence of internal defects or disease other than net necrosis was scored as a "+". All of the remaining tubers from lines which had all of the following qualities: 1) true to type by plant habit and tuber quality; 2) 25% or less foliar symptoms or significant reduction in symptoms (p=0.05); and 3) 2 or fewer tubers per line show net necrosis or 95% reduction of net compared to controls were bagged by plots and placed in storage for 60 days at which time this procedure was performed on the remaining tubers. All remaining tubers from wild type (RB) were also bagged and stored for later net analysis.

The results of the net necrosis analysis performed at harvest are shown in Table 2. This table combines the data from both test sites. For each line assayed 160 tubers were cut and rated for incidence of net necrosis. The 1600 tubers assayed from the 10 lines of Russet Burbank wild-type potato showed a total of 13.3% incidence of net necrosis (213 tubers) with a range of 7.5–19.4%, and 36.7% of the tubers (587 tubers) showed net necrosis plus other mild tuber discolorations. From pMON18685, (full length replicase coding sequence) 12 of the 24 lines assayed for net necrosis showed less symptoms than Russet Burbank wt lines with a total of 5.5% (106/1920) with net necrosis symptoms with a range of 2.5–7.5%, and 20.1% (386/1920) total discolorations. Seven lines of the 19 lines assayed from pMON18658 (3' replicase fragment, GDD) showed a combined incidence of net necrosis of 3.9% (44/1120) of the tubers with a range of 1.3–6.8%, and 18.4% (222/1120) of the tuber with any defects. Two of the 10 lines from pMON18643 (out of frame replicase sequence) had 6.9% (22/320) with net necrosis and 24.7% (79/320) with any defects. One line of 10 from pMON18644 (anti-sense) had 3.8% (6/160) with net necrosis symptoms and 25% (40/160) showed any defects. This assay showed that 12 of 24 lines from pMON18685 and 7 of 19 lines from pMON18658 had reduced incidence of net necrosis and lower incidence of other tuber discolorations at harvest. Two of 10 and 1 of 10 lines of pMON18643 and pMON18644, respectively, had reduced incidence of net necrosis. The sense constructs, pMON18685 and pMON18658, produced more lines with reduced net necrosis than pMON18643 and pMON18644, as a percent of the total lines assayed.

TABLE 2

| Net necrosis assay of replicase lines at harvest | | | | |
|---|---|---|---|---|
| Construct | #lines | necrosis/tubers | (% total, [range]) | other |
| RB wt | 10 | 213/1600 | (13.3%, [7.5–19.4]) | 587/1600 (36.7%) |

TABLE 2-continued Net necrosis assay of replicase lines at harvest

| Construct | #lines | necrosis/tubers | (% total, [range]) | other |
|---|---|---|---|---|
| pMON18685 | 12 | 106/1920 | (5.5%, [2.5–7.5]) | 386/1920 (20.1%) |
| pMON18658 | 7 | 44/112 | (3.9%, [1.3–6.8]) | 222/1120 (18.4%) |
| pMON18643 | 2 | 22/320 | (6.9%) | 79/320 (24.7%) |
| pMON18644 | 1 | 6/160 | (3.8%) | 40/160 (25%) |

The results of net necrosis assay of tubers after storage are shown in Table 3. Tubers were stored at 50°–55° F. for 2 months, then approximately 120 tubers/line per test site were cut as previously described to determine the incidence and severity of net necrosis symptoms. The data shown in Table 3 is from Test Site #2. The 10 lines from the Russet Burbank wild type (RBwt) lines averaged 11.4% net necrosis with a range of 2.6–31% per line. Five lines of pMON18685 were better than the controls for incidence of net necrosis after storage for a total of 0.8% incidence with a range of 0–1.4% net necrosis. Three lines of pMON18658 were better than the controls with a net necrosis incidence after storage of 1.1% with a range of 0–2.5%. The constructs pMON18643 and pMON18644 each had 1 line with reduced incidence of net necrosis after storage, with 0.8% and 3.0%, respectively. (Note: the data resulting from the net necrosis assay after storage is believed to have been skewed in favor of detecting less net necrosis due to the nature of the sampling process. Typically, at harvest the largest tubers were selected for the assay, leaving fewer large tubers for the assay after storage. Net necrosis occurs more often in the larger tuber samples than in the smaller. Hence, the data represented herein may in fact reflect that factor.)

TABLE 3

Net necrosis assay of replicase lines after storage

| Construct | # lines | necrosis/tubers | (% total, [range]) |
|---|---|---|---|
| RBwt | 10 | 137/1200 | (11.4%, [2.6–31]) |
| pMON18685 | 5 | 4/532 | (0.8%, [0–1.4]) |
| pMON18658 | 3 | 4/355 | (1.1%, [0–2.5]) |
| pMON18643 | 1 | 1/118 | (0.8%) |
| pMON18644 | 1 | 4/120 | (3.0%) |

G. ELISA of Leaf Tissue From Sprouted Tubers

The level of resistance can be measured by ELISA of leaf tissue obtained from sprouted tubers. The incidence of PLRV in sprouts from tubers is a reliable method for determining PLRV in tubers (Flanders et. al., (1990)). Low incidence of PLRV infection in the sprouts and low virus titer in tubers significantly impacts the incidence and severity of the net necrosis symptom. Additionally, potato plants which are highly resistant to infection and accumulation of PLRV in the tubers are more useful as seed material for commercial plantings.

The sprouting of tubers was obtained by cutting the rose end of approximately 40 tubers from each of the potato lines which had shown reduced foliar and net necrosis symptoms as well as Russet Burbank wild type (RBwt) and vector control lines (RBvc). Each potato piece had at least 3 eyes and was treated with a sprouting agent (gibberellic acid) then planted into soil in pots in a greenhouse. Six weeks post planting the eyes of each tuber had sprouted and a leaf sample was taken from each of 3 sprouts per tuber and pooled as one sample. The samples were homogenized in 750 µl PBS-T extraction buffer and 250 µl loaded into ELISA microtiter plates and assayed for the presence of PLRV with the reagents previously described.

The results of the assay of tubers sprouted after storage are shown in Table 4. The Russet Burbank wt and vc sprouts were highly infected with PLRV; on the average, 80% of the tubers assayed contained the virus. This is similar to the infection rate observed in Russet Burbank by Flanders et al. (1990). Five lines of pMON18685 (full length replicase) were highly resistant to tuber infection by PLRV as indicated by the extremely low incidence of PLRV in the sprouts. Four of the five lines had no detectable PLRV. Three lines from pMON18658 (GDD fragment) were assayed and shown to have reduced incidence of PLRV (17%). One line had no detectable PLRV. The single line of pMON18643 has a moderate incidence of PLRV (55%) and the single line of pMON18644 has a high level of PLRV (89%). We concluded from this data that the full-length PLRV replicase gene in pMON18685 confers near immunity to PLRV infection at a high frequency and pMON18658 with the GDD fragment also confers near immunity but at a lower frequency. The antisense construct pMON18644 was less effective for virus resistance and the out of frame translation initiation codon in pMON18643 adversely affects the production of the replicase gene product and reduces the efficacy of the construct for providing resistance to PLRV infection.

TABLE 4

Incidence of PLRV infection in tuber sprouts

| Construct | #lines | inf/tubers | (% total, [range]) |
|---|---|---|---|
| RBwt/RBvc | 5 | 160/200 | (80%, [72.5–90%]) |
| pMON18685 | 5 | 2/200 | (1%, [0–5%]) |
| pMON18658 | 3 | 20/120 | (17%, [0–27.5%]) |
| pMON18643 | 1 | 22/40 | (55%) |
| pMON18644 | 1 | 31/35 | (89%) |

H. Aphid Transmission Assay of PLRV from Field Inoculated Replicase lines

PLRV is not mechanically transmissible. Spread of PLRV from infected plants to uninfected plants can only be accomplished by aphids. This is the reason that insecticide application is currently necessary for controlling this disease. Virus resistant potatoes will no longer require insecticides to control aphids. Potato cultivars which are resistant to PLRV often display no or reduced titers of PLRV and the virus is not as easily transmitted from these plants to other plants by aphids. This characteristic is of commercial significance because it limits the potential for virus epidemics in the field.

Table 5 shows the results of aphid transmission of PLRV from leaves of field inoculated PLRV replicase lines to the indicator host *Physalis floridana*. Experimentally this is referred to as back transmission. The method used was: one young leaflet was harvested from each of ten plants from each of the replicase lines listed in Table 5. Five aphid were placed on each leaflet in a Petri dish on moist filter paper. After 24 hrs, each leaflet with aphids was placed on a young Physalis plant and covered with a cage. After 48 hrs, the aphids were killed by fumigation with nicotine sulfate. Symptoms of PLRV infection were scored 4 wks after inoculation. The 5 lines of pMON18685 which have shown low or no foliar symptoms, low or no tuber net necrosis and low or no virus in tuber sprouts also did not have aphid transmissible virus as shown in Table 5. The 3 lines of pMON18658 had low foliar symptoms, low tuber net necrosis and low virus in tuber sprouts, and did show some aphid transmissible virus.

In the lines we assayed, the antisense construct pMON18644 did not confer effective virus resistance, and the out of frame translation initiation codon in pMON18643 adversely affected the production of the replicase gene product and reduced the efficacy of the construct for providing resistance to PLRV.

TABLE 5

Back Transmission Assay

| Construct | #lines | #infected Physalis |
|---|---|---|
| pMON18685 | 5 | 0/50 |
| pMON18658 | 3 | 4/30 |

Note: Back transmission from PLRV infected Russet Burbank always end up with 90–100% of infected Physalis (Hassan et al., 1985), (Thomas, 1983 ).

All publications and patent applications mentioned in this specification are indicative of the level of skill of those skilled in the art to which this invention pertains.

From the foregoing, it will be seen that this invention is one well adapted to attain all the ends and objects hereinabove set forth together with advantages that are obvious and that are inherent to the invention. It will be understood that certain features and sub-combinations are of utility and can be employed without reference to other features and sub-combinations. This is contemplated by and is within the scope of the claims. Because many possible embodiments can be made of the invention without departing from the scope thereof, it is to be understood that all matter herein set forth or shown in the accompanying drawings is to be interpreted as illustrative and not in a limiting sense.

BIBLIOGRAPHY

Abel et al. (1986). *Science* 232: 738–743.
Bahner et al. (1990). *J. of Gen. Virol.* 71:2251–2257.
Bevan et. al., (1984). *Nucl. Acids Res.* 12: 8711–8721.
Bol, et. al., (1990). *Ann. Rev. Phytopath.* 28:113.
Braun et. al., (1992). *Plant Cell,* 4:735–744.
Carr et. al., (1992). *Mol Plant Microbe Interactions,* 5:397–404.
Cooper et. al., (1983). *Phytopathology* 73:127–128.
Coruzzi et. al., (1984). *EMBO* 3: 1671–1679.
Cuozzo et. al., (1988). *BioTechnol.* 6: 549–557.
Ditta et. al., (1980). *Proc. Natl. Acad. Sci. USA* 77: 7347–7351.
Flanders et al. (1990). *Amer. Pot. J.* 67: 589–602.
Fling et. al., (1985). *Nucl. Acids Res.* 13: 7095–7106.
Fraley et. al., (1983). *Proc. Natl. Acad. Sci. USA* 80: 4803–4807.
Golemboski et. al., (1990). *Proc. Natl. Acad. Sci. USA* 87: 6311–6315.
Gorbalenya et. al., (1988). *Nature* 333:22.
Habili et. al., (1989). *Nucleic Acids Res.* 17: 9543–9555.
Harrison, et. al., (1987). *Nature* 328: 799.
Hassan et al., (1985) *Phytopath.,* 75, 287–291.
Hemenway et. al., (1988). *EMBO J.* 7: 1273–1280.
Herrera-Estrella et. al., (1983). *Nature* 303: 209.
Hiatt, (1990). *Agbiotech News Information* 2: 687.
Hodgman et. al., (1988). *Nature* 333: 22–23.
Irvin, et. al., (1980). *Arch. Biochem Biophys.* 200: 418.
Ishikawa et. al., (1986). *Nucleic Acids Res.* 14: 8291–8305.
Kamer et. al., (1984). *Nucleic Acid Res.* 12: 7269–7282.
Kaniewski et. al., (1990). *Biotechnol.* 8:750–754.
Klee et. al., (1985). *BioTechnol.* 3: 637–642.
Koncz et. al., (1986). *Mol. Gen. Genet.* 204: 383–396.
Koonin, (1990). *J. of Gen. Virol.* 72: 2197–2206.
Lawson et. al., (1990) *BioTechnol.* 8: 127–134.
Lutcke et. al., (1987) *EMBO J.* 6:43–48.
Martin et. al., (1990). *Annu. Rev. Phytopathol.,*28:341–363.
Mayo et. al., (1982). *J. Gen. Virol.* 59: 163–167.
Mayo et. al., (1989). *J. Gen. Virol.* 70: 1037–1051.
Morch (1987). *Nucleic Acids Res.* 15: 4123.
Murry et. al., (1989). *NAR* 17:477–498.
Odell et. al., (1985). *Nature* 313: 810–812.
Perlak et al. , (1991), *Proc. Natl. Acad. Sci. USA* 88: 3324–3328.
Prüfer et. al., (1992). *EMBO Journal* 11: 1111–1117.
Sanger et. al., (1977). *Proc. Natl. Acad. Sci. USA* 74: 5463–5467.
Shepardson, et. al., (1980). *Virology* 105:379–392.
Stalker et. al., (1981). *Mol. Gen. Genet.* 181: 8–12.
Stark et. al., (1989). *BioTechnol.* 7: 1257–1262.
Tacke et. al., (1991). *Jou. Gen. Virol.,* 72: 2035–2038.
Taschner et. al., (1991). *Virology* 181: 445–450.
Thomas et al., *Plant Physiology,* 67, 744–747.
Tumer et. al.,(1987). *EMBO J.* 6:1181–1188.
Walbot, et. al., (1988). *Nature* 334: 196.
van der Wilk et. al., (1989). *FEBS Letters* 245: 51–56.
van Dun et. al., (1988 -A). *Virology* 163: 572–578.
van Dun et. al., (1988). *Virology* 164: 383–389.

We claim:

1. A DNA molecule which comprises:

(a) a promoter region which functions in plant cells to cause the production of an RNA sequence; which is operably linked to (b) a structural gene encoding a full length potato leafroll virus replicase; which is operably linked to (c) a 3' non-translated region which functions in plant cells to cause the termination of transcription and the addition of polyadenylated ribonucleotides to the 3' end of the transcribed mRNA sequence.

2. A DNA molecule according to claim 1 wherein said promoter region is selected from the group consisting of the FMV35S promoter region, the CaMV35S promoter region, and the enhanced CaMV35S promoter region.

3. A DNA molecule according to claim 2 wherein said promoter region is a FMV promoter region.

4. A DNA molecule according to claim 1 wherein said structural gene consists of nucleotides 38–3,901 of SEQ ID NO. 1.

5. A DNA molecule according to claim 1 wherein said 3' non-translated region is selected from the group consisting of the 3' non-translated regions from the nopaline synthase (NOS) genes, the soybean 7S storage protein genes, and the pea small subunit of the ribulose 1,5-bisphosphate carboxylase-oxygenase (ssRUBISCO) E9 genes.

6. A DNA molecule according to claim 5 wherein said 3' non-translated region is from the pea small subunit of the ribulose 1,5-bisphosphate carboxylase-oxygenase (ssRUBISCO) E9 genes.

7. A method for providing resistance to infection by potato leafroll virus in a susceptible Solanaceae plant which comprises:

(a) transforming plant cells with a DNA molecule which comprises:

(i) a promoter region which functions in plant cells to cause the production of an RNA sequence; which is operably linked to (ii) a structural gene encoding a full length potato leafroll virus replicase; which is operably linked to (iii) a 3' non-translated region which functions in plant cells to cause the termination of transcription and the addition of polyadenylated ribonucleotides to the 3' end of the transcribed mRNA sequence;

(b) regenerating said plant cells to provide a differentiated plant; and (c) selecting a transformed plant which expresses the full length potato leafroll virus replicase gene at a level sufficient to render the plant resistant to infection by said potato leafroll virus.

8. A method according to claim 7 wherein said plant is selected from the group consisting of potato, tomato, and tobacco.

9. A method according to claim 8 wherein said potato is selected from the group consisting of Russet Burbank, Shepody, Atlantic, Norchip, and Superior.

10. A method according to claim 9 wherein said potato is Russett Burbank.

11. A method according to claim 7 wherein said promoter is selected from the group consisting of the FMV35S promoter region, the CaMV35S promoter region, and the enhanced CaMV35S promoter region.

12. A method according to claim 7 wherein said structural gene consists of nucleotides 38–3,901 of SEQ ID NO. 1.

13. A method according to claim 7 wherein said 3' non-translated region is selected from the group consisting of the 3' non-translated regions from the nopaline synthase (NOS) genes, the soybean 7S storage protein genes, and the pea small subunit of the ribulose 1,5-bisphosphate carboxylase-oxygenase (ssRUBISCO) E9 genes.

14. A method for providing reduction in net necrosis resulting from infection by potato leafroll virus in a susceptible Solanaceae plant which comprises:
   (a) transforming plant cells with a DNA molecule which comprises:
      (i) a promoter region which functions in plant cells to cause the production of an RNA sequence; which is operably linked to
      (ii) a structural gene encoding a full length potato leafroll virus replicase; which is operably linked to
      (iii) a 3' non-translated region which functions in plant cells to cause the termination of transcription and the addition of polyadenylated ribonucleotides to the 3' end of the transcribed mRNA sequence;
   (b) regenerating said plant cells to provide a differentiated plant; and
   (c) selecting a transformed plant which expresses the full length potato leafroll virus replicase gene at a level sufficient to render the plant resistant to infection by said potato leafroll virus.

15. A method according to claim 14 wherein said plant is selected from the group consisting of potato, tomato, and tobacco.

16. A method according to claim 15 wherein said potato is selected from the group consisting of Russet Burbank, Shepody, Atlantic, Norchip, and Superior.

17. A method according to claim 15 wherein said potato is Russett Burbank.

18. A method according to claim 14 wherein said promoter is selected from the group consisting of the FMV35S promoter region, the CaMV35S promoter region, and the enhanced CaMV35S promoter region.

19. A method according to claim 14 wherein said structural gene consists of nucleotides 38–3,901 of SEQ ID NO. 1.

20. A method according to claim 14 wherein said 3' non-translated region is selected from the group consisting of the 3' non-translated regions from the nopaline synthase (NOS) genes, the soybean 7S storage protein genes, and the pea small subunit of the ribulose 1,5-bisphosphate carboxylase-oxygenase (ssRUBISCO) E9 genes.

21. A virus resistant transformed Solanaceae plant which contains in its genome a DNA molecule which comprises:
   (a) a promoter region which functions in plant cells to cause the production of an RNA sequence; which is operably linked to
   (b) a structural gene encoding a full length potato leafroll virus replicase; which is operably linked to
   (c) a 3' non-translated region which functions in plant cells to cause the termination of transcription and the addition of polyadenylated ribonucleotides to the 3' end of the transcribed mRNA sequence.

* * * * *